United States Patent
Dagdeviren et al.

(10) Patent No.: US 10,137,306 B2
(45) Date of Patent: Nov. 27, 2018

(54) MATERIALS, DEVICES AND SYSTEMS FOR PIEZOELECTRIC ENERGY HARVESTING AND STORAGE

(71) Applicants: The Arizona Board of Regents on behalf of The University of Arizona, Tucson, AZ (US); The Board of Trustees of the University of Illinois, Urbana, IL (US)

(72) Inventors: Canan Dagdeviren, Cambridge, MA (US); John A. Rogers, Champaign, IL (US); Marvin J. Slepian, Tucson, AZ (US)

(73) Assignees: The Arizona Board of Regents on Behalf of The University of Arizona, Tucson, AZ (US); The Board of Trustees of The University of Illinois, Urbana, IL (US)

( * ) Notice: Subject to any disclaimer, the term of this patent is extended or adjusted under 35 U.S.C. 154(b) by 48 days.

(21) Appl. No.: 15/111,447

(22) PCT Filed: Jan. 13, 2015

(86) PCT No.: PCT/US2015/011245
§ 371 (c)(1),
(2) Date: Jul. 13, 2016

(87) PCT Pub. No.: WO2015/106282
PCT Pub. Date: Jul. 16, 2015

(65) Prior Publication Data
US 2016/0346556 A1    Dec. 1, 2016

Related U.S. Application Data

(60) Provisional application No. 61/926,841, filed on Jan. 13, 2014.

(51) Int. Cl.
*A61N 1/378* (2006.01)
*H01L 41/18* (2006.01)
(Continued)

(52) U.S. Cl.
CPC .......... *A61N 1/3785* (2013.01); *H01L 41/081* (2013.01); *H01L 41/113* (2013.01);
(Continued)

(58) Field of Classification Search
None
See application file for complete search history.

(56) References Cited

U.S. PATENT DOCUMENTS 8,552,299 B2   10/2013   Rogers
2004/0123946 A1*  7/2004   Cass ...................... B29C 70/20
                                                              156/296
(Continued)

OTHER PUBLICATIONS

Chen, et al., "1.6 V Nanogenerator for mechanical energy harvesting using PZT nanofibers", Nano Lett., 10: 2133-7 (2010).
(Continued)

*Primary Examiner* — Brian T Gedeon
(74) *Attorney, Agent, or Firm* — Pabst Patent Group LLP

(57) ABSTRACT

Materials and systems that enable high efficiency conversion of mechanical stress to electrical energy and methods of use thereof are described herein. The materials and systems are preferably used to provide power to medical devices implanted inside or used outside of a patient's body. For medical devices, the materials and systems convert electrical energy from the natural contractile and relaxation motion of a portion of a patient's body, such as the heart, lung and diaphragm, or via motion of body materials or fluids such as air, blood, urine, or stool. The materials and systems are capable of being bent, folded or otherwise stressed without fracturing and include piezoelectric materials on a flexible substrate. The materials and systems are preferably fash-
(Continued)

ioned to be generally conformal with intimate apposition to complex surface topographies.

21 Claims, 18 Drawing Sheets

(51) Int. Cl.
  *H02N 2/18* (2006.01)
  *H01L 41/08* (2006.01)
  *H01L 41/113* (2006.01)
  *H01L 41/312* (2013.01)

(52) U.S. Cl.
  CPC ............... *H01L 41/18* (2013.01); *H02N 2/18* (2013.01); *H02N 2/181* (2013.01); *H02N 2/186* (2013.01); *A61B 2560/0214* (2013.01); *H01L 41/312* (2013.01)

(56) References Cited

U.S. PATENT DOCUMENTS

| | | | |
|---|---|---|---|
| 2008/0055581 A1 | 3/2008 | Rogers | |
| 2011/0071774 A1 | 3/2011 | Fonda | |
| 2011/0109203 A1* | 5/2011 | McAlpine | H01L 41/314 310/345 |
| 2011/0275947 A1 | 11/2011 | Feldman | |
| 2012/0312456 A1 | 12/2012 | McAlpine | |
| 2013/0140649 A1* | 6/2013 | Rogers | H01L 29/66 257/414 |
| 2013/0334930 A1 | 12/2013 | Kang | |

OTHER PUBLICATIONS

Choi, et al., "Ferroelectric and Piezoelectric Properties of Highly Oriented Pb(Zr,Ti)O3 Film Grown on Pt/Ti/SiO2/Si Substrate Using Conductive Lanthanum Nickel Nitrate Buffer Layer" ,. J. Mater. Res., 20: 726-33 ( 2005).

Cuadras, et al., "Thermal energy harvesting through pyroelectricity" , Sens Actuators A Phys., 158:132-139 (2010).

Dagdeviren , et al., "Transient, biocompatible electronics and energy harvesters based onZnO" , Small, 9(20):3398-3404 (2013).

Damjanovic, "Ferroelectric, Dielectric and Piezoelectric Properties of Ferroelectric Thin Films and Ceramics," Rep. Prog. Phys., 61: 1267-1324 (1998).

Energy Harvesting, Wikipedia encyclopedia, downloaded from the internet, last modified Apr. 23, 2011.

Halámková•, et al.,"Implanted biofuel cell operating in living snail" , J. Am. Chem. Soc., 134:5040-3 (2012).

International Search Report znd Written Opinion for PCT application PCT/US2015/011245 dated Apr. 2, 2015.

Karami and Inman, "Equivalent damping and frequency change for linear and nonlinear hybrid vibrational energy harvesting systems" , J. Sound Vib., 330:5583-97 (2011).

Karami and Inman, "Powering pacemakers from heartbeat vibrations using linear and nonlinear energy harvesters" , Appl. Phys. Lett., 100:042901 (2012).

Kerzenmacher, et al., "Energy harvesting by implantable abiotically catalyzed glucose fuel cells" , J. Power Sources, 182:1-17 (2008).

Liang, et al., "Phase transformation of poly (vinylidene diflouride) in energy harvesting" , J Mater Res., 26(1):1-8 (2011).

Mallela, et al., "Trends in cardiac pacemaker batteries" , Indian Pacing Electrophysiol. J., 4:201-212 (2004).

Mateu and Moll, "Review of energy harvesting techniques and applications for microelectronics" , Proc SPIE, 5837:359-373 (2005).

Mercier, et al., "Energy extraction from the biologic battery in the inner ear" , Nat. Biotechnology, 30: 1240-1243 (2012).

Muralt, "Piezoelectric Thin Films for MEMS" , Integr. Ferroelectr., 17: 297-307 (1997).

Nguyen, et al., "Piezoelectric nanoribbons for monitoring cellular deformations" , Nature Nanotech., 7:587-93 (2012).

Park, et al., "Piezoelectric BaTiO3 thin film nanogenerator on plastic substrates" Nano Lett 10(12):4939-43 (2010).

Persano, et al., "High performance piezoelectric devices based on aligned arrays of nanofibers of poly(vinylidenefluoride-co-trifluoroethylene)." ,Nature Comm., 4:1633. doi: 10.1038 (2013).

Pfenniger, et al., "Energy harvesting through arterial wall deformation: design considerations for a magneto-hydrodynamic generator" , Med. Biol. Eng. Comput., 51 (7):741-755 (2013).

Polla and Francis, "Processing and Characterization of Piezoelectric Materials and Integration into Microelectromechanical Systems" , Annu. Rev. Mater. Sci., 28:563-97 (1998).

Qi, et al., "Enhanced piezoelectricity and stretchability in energy harvesting devices fabricated from buckled PZT ribbons" , Nano Lett., 11:1331-6 (2011).

Reynolds, "Utilization of bioelectricity as power supply for implanted electronic devices" , Aerosp. Med., 35:115-117 (1964).

Starner, "Human-powered wearable computing" , IBM Systems J., 35 (3&4):618-29 (1996).

Wang and Song, "Piezoelectric nanogenerator based on zinc oxide nanowire arrays" , Science, 213:242-246 (2006).

Wang, et al., "Direct current nanogenerator driven by ultrasonic wave" , Science, 316:102-105 (2007).

Wischke, et al., "Piezoelectrically tunable electromagnetic vibration harvester" , J. Micromech. Microeng., 20(3):035025 (2010).

Wong, et al., "A very low-power CMOS mixed-signal IC for implantable pacemaker applications" , IEEE J Solid-State Circuits, 39:2446-2456 (2004).

Xu, et al., "Integrated multilayer nanogenerator fabricated using paired nanotip-to-nanowire brushes" , Nano Lett., 8:4027-4032 (2008).

Zhu, et al., "Flexible high-output nanogenerator based on lateral ZnO nanowire array" , Nano Lett., 10:3151-3155 (2010).

Zurbuchen, et al., "Energy harvesting from the beating heart by a mass imbalance oscillation generator" , Annals of Biomed. Eng., 41(1):131-141 (2013).

* cited by examiner

MATERIALS, DEVICES AND SYSTEMS FOR PIEZOELECTRIC ENERGY HARVESTING AND STORAGE

CROSS-REFERENCE TO RELATED APPLICATIONS

This application is a 371 application of International Application No. PCT/US2015/011245 filed Jan. 13, 2015, which claims benefit of U.S. Provisional Application No. 61/926,841, filed Jan. 13, 2014.

STATEMENT REGARDING FEDERALLY SPONSORED RESEARCH OR DEVELOPMENT

This invention was made with government support under DE-FG02-07ER464741, awarded by DOE. The government has certain rights in the invention.

FIELD OF THE INVENTION

The invention is generally directed to devices for energy harvesting and storage, particularly for use with medical devices.

BACKGROUND OF THE INVENTION

Nearly all classes of active wearable and implantable biomedical devices rely on some form of battery power for operation. Heart rate monitors, pacemakers, implantable cardioverter-defibrillators and neural stimulators together represent a broad subset of bio-electronic devices that provide continuous diagnostics and therapy in this mode. Although advances in battery technology have led to substantial reductions in overall sizes and increases in storage capacities, operational lifetimes remain limited, rarely exceeding a few days for wearable devices and a few years for implants (Karami & Inman, "Powering pacemakers from heartbeat vibrations using linear and nonlinear energy harvesters", *Appl. Phys. Lett.,* 100:042901 (2012); Kerzenmacher, et al., "Energy harvesting by implantable abiotically catalyzed glucose fuel cells", *J. Power Sources,* 182:1-17 (2008); Mateu & Moll, "Review of energy harvesting techniques and applications for microelectronics", *Proc SPIE,* 5837:359-373 (2005)). Surgical procedures to replace the depleted batteries of implantable devices are thus essential, exposing patients to health risks, heightened morbidity and even potential mortality (Mallela, et al., "Trends in cardiac pacemaker batteries", *Indian Pacing Electrophysiol.* 1, 4:201-212 (2004)). The health burden and costs are substantial.

Investigations into energy harvesting strategies to replace batteries demonstrate several unusual ways to extract power from chemical, mechanical, electrical and thermal processes in the human body (Starner, "Human-powered wearable computing", *IBM Systems J,* 35 (3&4):618-629 (1996)). Examples include use of glucose oxidation (Kerzenmacher 2008; Halamkova, et al., "Implanted biofuel cell operating in living snail", *J. Am. Chem. Soc.,* 134:5040-5043 (2012)), temperature gradients (Cuadras, et al., "Thermal energy harvesting through pyroelectricity", *Sens Actuators A Phys.,* 158:132-139 (2010)), chemical energy via biogalvanic cells (Reynolds L W, "Utilization of bioelectricity as power supply for implanted electronic devices", *Aerosp. Med.,* 35:115-117 (1964)), electric potentials of the inner ear (Mercier, et al., "Energy extraction from the biologic battery in the inner ear", *Nat. Biotechnology,* 30: 1240-1243 (2012)), mechanical movements of limbs and natural vibrations of internal organs (Wischke, et al., "Piezoelectrically tunable electromagnetic vibration harvester", *J. Micromech. Microeng.,* 20(3):035025 (2010); Wong L S, et al., "A very low-power CMOS mixed-signal IC for implantable pacemaker applications", *IEEE J Solid-State Circuits,* 39:2446-2456 (2004)). Such phenomena provide promising opportunities for power supply to wearable and implantable devices that interface with the body. A recent example involves a hybrid kinetic device integrated with the heart for applications with pacemakers (Zurbuchen A, et al., "Energy harvesting from the beating heart by a mass imbalance oscillation generator", *Annals of Biomed. Eng.,* 41(1):131-141 (2013)). More speculative approaches, based on analytical models of harvesting from pressure-driven deformations of an artery by magneto-hydrodynamics, also exist (Pfenniger, et al., "Energy harvesting through arterial wall deformation: design considerations for a magneto-hydrodynamic generator", *Med. Biol. Eng. Comput.,* 51(7):741-755 (2013)).

Cardiac and lung motions, in particular, serve as inexhaustible sources of energy during the lifespan of a patient. Mechanical to electrical transduction mechanisms in piezoelectric materials may offer viable routes to energy harvesting in such cases. Proposals exist for devices that convert heartbeat vibrations into electrical energy using resonantly coupled motions of thick (1-2 mm) piezoelectric ceramic beams on brass substrates (Karami (2012); Karami & Inman, "Equivalent damping and frequency change for linear and nonlinear hybrid vibrational energy harvesting systems", *J. Sound Vib.,* 330:5583-5597 (2011)).

While such models highlight the potential for self-powering devices, there are important practical challenges in the coupling of rigid mechanical systems with the soft, dynamic surfaces of the body in a manner that does not induce adverse side effects. Piezoelectric materials are rigid materials that could restrict movement of the tissue to which they are attached. Flexible devices based on arrays of piezoelectric ZnO nanowires (NWs) are being developed (Wang, et al., "Direct current nanogenerator driven by ultrasonic wave", *Science,* 316:102-105 (2007); Song & Wang, "Piezoelectric nanogenerator based on zinc oxide nanowire arrays", *Science,* 213:242-246 (2006); Xu, et al., "Integrated multilayer nanogenerator fabricated using paired nanotip-to-nanowire brushes", *Nano Lett.,* 8:4027-4032 (2008)). Experiments performed with a linear motor to periodically deform the device indicate electrical outputs as large as 1-2 V (open-circuit voltage) and 100 nA (short-circuit current) (Zhu, et al., "Flexible high-output nanogenerator based on lateral ZnO nanowire array", *Nano Lett.,* 10:3151-3155 (2010)). Initial in vivo tests on rabbit hearts yielded voltages and currents of ~1 mV and ~1 pA, respectively. However, the associated electrical power is substantially less than that required for operation of existing classes of implants, such as pacemakers. Some improvement in performance is possible with thin film geometries, as demonstrated in bending experiments on devices based on $BaTiO_3$ (Park, et al., "Piezoelectric $BaTiO_3$ thin film nanogenerator on plastic substrates", Nano Lett 10:4939 (2010)) and PZT (Chen, et al., "1.6 V Nanogenerator for mechanical energy harvesting using PZT nanofibers", *Nano Lett.,* 10: 2133-2137 (2010); Qi, et al., "Enhanced piezoelectricity and stretchability in energy harvesting devices fabricated from buckled PZT ribbons", *Nano Lett.,* 11:1331-1336 (2011)).

However, there is a need to develop materials and devices that generate greater amounts of power.

Therefore, it is an object of the invention to provide improved materials, devices, and/or systems for generating, and optionally storing and/or telemetering electrical power sufficient to power medical or other devices without requiring replacement of the battery.

It is a further object of the invention to provide improved methods for powering devices, particularly medical devices.

SUMMARY OF THE INVENTION

Materials and systems that enable high efficiency conversion of mechanical energy to electrical energy and methods of use thereof are described herein. The materials and systems are preferably used to provide power to medical devices implanted inside or used outside of a patient's body. For medical devices, the materials and systems convert electrical energy from the natural contractile and relaxation motion of a portion of a patient's body, such as the heart, lung and diaphragm, or via motion of body materials or fluids such as air, blood, urine, or stool. The materials are capable of being bent, folded or otherwise stressed without fracturing and include piezoelectric materials on a flexible substrate. The materials are preferably fashioned to be generally conformal with intimate apposition to complex tissue surface topographies.

The system may contain a single layer of the energy harvesting material. Preferably the system contains multiple layers of the energy harvesting material, more preferably in combination with one or more rectifiers and/or batteries.

The effectiveness of the materials and systems was demonstrated in several different in vitro models as well as in vivo animal models, each of which has organs with sizes that approach human scales. A co-integrated collection of such energy harvesting elements with rectifiers and microbatteries provides an entire flexible system, capable of viable integration with the beating heart via medical sutures and operation with efficiencies of ~2%. Additional experiments, computational models and results in multilayer configurations describe the behaviors and properties of these devices, illuminate exemplary configurations that offer sufficient power outputs for operation of pacemakers, with or without battery assist.

BRIEF DESCRIPTION OF THE DRAWINGS

FIG. 1A is a schematic illustration of array of ribbons of PZT in a capacitor structure on a $SiO_2$/Si wafer. A cross sectional view of one element in this array appears on the right (FIG. 1D). FIG. 1B illustrates the pattern of photoresist on the array, and FIG. 1E illustrates a cross section of one element during undercut etching with dilute HF solution. FIG. 1C illustrates how retrieving the array with a PDMS stamp to leave them adhered to the surface of the stamp. FIG. 1F illustrates the result after transfer printing onto a flexible film of PI. ($x_1$ direction, from left to right; $x_2$ direction, from top to bottom)

FIG. 2A is a schematic illustration of the theoretical shape for buckling of a PZT MEH under compression. FIGS. 2B and 2C contain two views of a single PZT ribbon capacitor structure: the top view (FIG. 2B), and a cross sectional view showing position of the neutral mechanical plane of the device (FIG. 2C).

FIG. 3A illustrates 3D FEM modeling for the device. The results highlighted by the black dashed box give the computed distributions of strain in the PZT ribbons for a displacement load of 5 mm along the horizontal direction. FIGS. 3B-3D depict experimental and theoretical results for displacement ($\Delta L$=10 mm, 5 mm, 3 mm, and 1.5 mm) (FIG. 3B), voltage(V) (FIG. 3C), and current ($\mu A$) (FIG. 3D) as a function of time for PZT MEHs under bending loads similar to those shown in FIG. 3A. FIG. 3E is a schematic illustration of a PZT MEH connected to and co-integrated with a rectifier and rechargeable microbattery. A circuit schematic is also provided. FIG. 3F is a line graph of Voltage across such a battery as a function of time during charging by a PZT MEH under cyclic bending load. FIG. 3G is a line graph of the peak voltage output of the PZT MEH is 4.5 V. The circled portion in the lower left area of the graph is highlighted (magnified) in the graft of FIG. 3G. The results highlight the expected stepwise behavior in charging.

FIGS. 5A-5F are graphs depicting open circuit voltage as a function of time for PZT MEHs on bovine (FIGS. 5A, 5B and 5C) and ovine (FIGS. 5D, 5E and 5F) hearts, mounted on RV (FIGS. 5A and 5D), LV (FIGS. 5B and 5E), and free wall (FIGS. 5C and 5F) at an orientation of 0° relative to the apex of the heart. The heart rate is 80 beats/min FIG. 5G is a graph illustrating the measurements of maximum values of the peak open circuit voltages produced by these devices indicating peak output at 45°. FIG. 5H is a bar graph illustrating average peak voltages of a PZT MEH on the RV of a bovine heart at 0°, for various heart rate (80-120 beats/min) controlled by a temporary pacemaker. FIG. 5I is a graph showing the maximum peak voltage for various dosages of dobutamine infusion, for the case of a device on the RV (open points) and LV (shaded points) of a bovine heart, at 0°. FIGS. 5J-5K are two graphs showing the voltage as a function of time for PZT MEHs on the LV (FIG. 5J) and RV (FIG. 5K) of a bovine heart, with a base and maximum dose of dobutamine.

FIGS. 7A-7B shows the voltage as a function of time for such devices on the bovine (FIG. 7A) and ovine (FIG. 7B) lung. FIGS. 7C-7D show plots corresponding to the regions indicated by the dashed lines in (FIG. 7A) and (FIG. 7B), respectively. FIGS. 7E-7F shows the voltage as a function of time for such a device on the bovine (FIG. 7E) and ovine (FIG. 7F) diaphragm.

FIG. 11A shows a schematic illustration of a multilayer stack of five independent PZT MEHs connected in series. A circuit schematic appears in the top right. FIG. 11B shows a schematic illustration of the theoretical shape for buckling of a stack of PZT MEHs with spin-cast layers of silicone elastomer (thickness 10 μm) in between, under compression. FIG. 11C shows a time-averaged power density as a function of the bending load displacement (E: experimental data, T: theory) for stacks consisting of one (bottom curve), three (middle curve) and five (top curve) PZT MEHs, connected in series (in vitro tests).

DETAILED DESCRIPTION OF THE INVENTION

I. Definitions

Figure 1A:
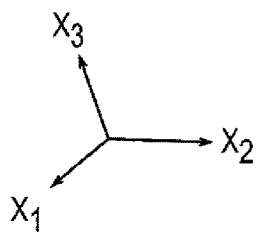
FIGS. 1A-1F are schematics illustrating procedures for fabricating a PZT MEH on a polyimide (PI) substrate.
Figure 1A:
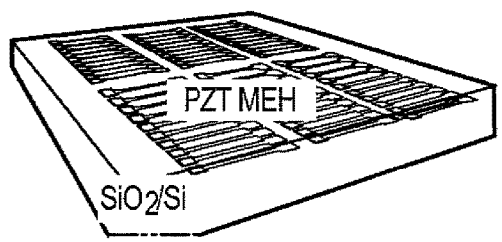
Figure 1D:
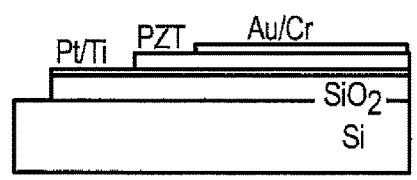
Figure 1B:
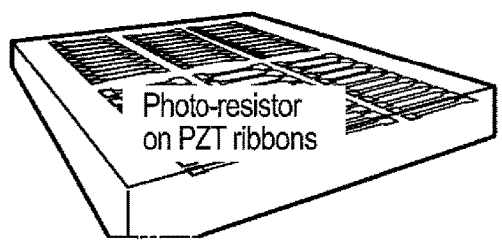
Figure 1E:
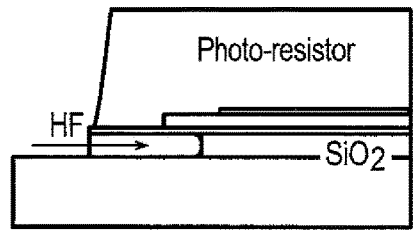
Figure 1C:
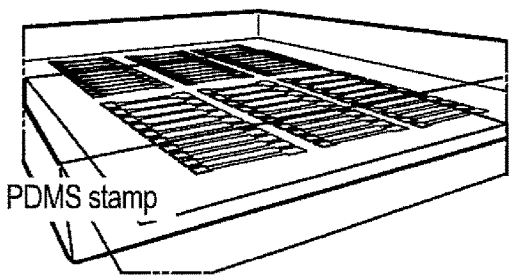

The terms "foldable", "flexible" and "bendable" are used synonymously herein and refer to the ability of a material, structure, device, or device component to be deformed into a curved shape without undergoing a transformation that introduces significant strain, such as strain characterizing the failure point of a material, structure, device, or device component. In an exemplary embodiment, a flexible material, structure, device or device component may be deformed into a curved shape without introducing strain larger than or equal to about 5%, preferably for some applications larger than or equal to about 1%, and more preferably for some applications larger than or equal to about 0.5% in strain-sensitive regions.

"Stretchable" refers to the ability of a material, structure, device, or device component to be strained without undergoing fracture. In an exemplary embodiment, a stretchable material, structure, device, or device component may undergo strain larger than about 0.5% without fracturing, preferably for some applications strain larger than about 1% without fracturing and more preferably for some applications strain larger than about 3% without fracturing.

"Ultrathin" refers to devices or device components, such as a material included therein, of thin geometries that exhibit extreme levels of bendability. A substrate material that is ultrathin has a thickness of 100 μm or less. Optionally, the thickness of an ultrathin material may be 50 μm or less, or 10 μm or less.

"Conformal" refers to the ability of a material or construct to assume intimate contact with an underlying complex surface topography to which it is applied.

"Efficiency" is generally used to refer to conversion of mechanical stress to electrical energy. Efficiency can be calculated as follows: total mechanical work is the product of the number of cycles for a battery's voltage to saturate (e.g., 7,500 cycles for $\Delta L_{max}=10$ mm) and work done in each cycle $$\int_0^{\Delta L_{max}} F d\Delta L,$$

where $F=4\pi^2 w_{PI}\overline{EI}_{PI}/L^2$ is the bucking force, and $w_{PI}$ is the width.

II. Flexible Energy Harvesting Materials

The energy harvesting material contains a sufficient amount of the flexible substrate material in a suitable configuration to retain the flexibility of the energy harvesting material, while also containing a sufficient amount and suitable orientation of the piezoelectric material to enable high efficiency conversion of mechanical energy to electrical energy.

As shown in the Examples, the energy harvesting material and any device incorporating or containing one or more energy harvesting materials are stable and able to produce electrical energy regardless of its location on the heart, even when repeatedly subjected to extensive stress and strain.

The mechanical energy harvester typically has an efficiency of at least 1%, preferably at least 1.5%, preferably approximately, 2% or greater, for the conversion of applied mechanical stress to electrical energy. This value can be improved by decreasing the thicknesses and Young's moduli of the electrodes, encapsulation layer, and/or by increasing the area coverage of the piezoelectric material. Reductions in viscoelastic dissipation of the flexible substrate material can also be helpful. Dagdeviren C, et al., "Transient, biocompatible electronics and energy harvesters based on ZnO", *Small,* 9(20):3398-3404 (2013).

In a preferred embodiment the energy harvesting material contains discrete areas or regions of piezoelectric material, typically ranging in size from about 150 cm to 1 cm, interspersed in a flexible substrate material. In an alternative embodiment, the energy harvesting material is a continuum, with the piezoelectric materials effectively seamlessly integrated into the flexible substrate material. Methods for making these materials are known to one of ordinary skill in the art. See, e.g., Wang X D, Song J H, Liu J, Wang Z L "Direct current nanogenerator driven by ultrasonic wave", *Science,* 316:102-105 (2007); and Chen, et al., "1.6 V Nanogenerator for mechanical energy harvesting using PZT nanofibers," *Nano Lett,* 10: 2133-2137 (2010). The disclosures of these references are incorporated herein by reference.

The piezoelectric material is typically in contact (placed on top of) a relatively stiff material with a high Young's modulus to allow for a high voltage output. A low modulus material is configured to be in contact with the biological surface or non-biological surface (e.g. surface of a second device or machine). Thus the energy harvesting material is typically a heterogeneous integration of high and low modulus materials.

The piezoelectric material(s) may contain a single layer or multiple layers. Similarly, the flexible substrate material may contain one layer or multiple layers.

In one embodiment, the energy harvesting material contains a ribbon of the piezoelectric material in a flexible substrate, preferably a substrate with a low Young's modulus.

The energy harvesting material can be combined with one or more additional energy harvesting materials to form a group of energy harvesting materials, where each energy harvesting material contains both the piezoelectric materials and the flexible substrate material. The group may be configured in the form of a stack with each material connected to the next material in the group in parallel. Each group contains at least 2, 3, 4, 5, 6, 7, 8, 9, 10, or more energy harvesting materials.

In another embodiment, higher numbers of ribbons in a group are used, e.g. 20, 50, etc. The group may be configuration as "bundles of stacks," i.e. group forms a stack, then these may be layered or otherwise assembled as a collective. There may be or may not be a separating, insulating, or flexibility later between bundles.

The number of energy harvesting materials in a given group may be the same as or different from the number of energy harvesting materials in another group in the same device.

Each group may be connected to the next group in series. By connecting the groups in series, the voltage of the resulting system can be increased. An energy harvesting device may contain at least 2 groups in series, preferably it contains more than 2 groups in series, such as at least 3, 4, 5, 6, 7, 8, 9, 10, 11, 12, 13, 14, 15, 16, 17, 19, 19, 20 or more groups of energy harvesting materials connected to each other in series. In another embodiment, higher numbers of groups are used in series, for example to generate more power. The stacks may be layered or bundled in parallel, criss-cross, or at other angles. The stacks can be arranged in a circular fashion on in 3-D as a sphere or other prismatic geometric shape.

The piezoelectric materials are generally distributed throughout the energy harvesting material and physically connected to each other by the flexible substrate material with maintained electrical interconnects as well.

The piezoelectric materials are encapsulated in an inert, flexible, biocompatible plastic, such as polyimide (PI).

A. Properties of Energy Harvesting Material i. Harvesting of Energy

Preferably, for implantable, medical devices, the energy harvesting material or a system comprising one or more, preferably a plurality of, energy harvesting materials, generates a sufficient amount of electrical energy to power the device over the lifespan of the device (e.g. for at least 10 years or beyond 10 years, such as for at least 15 years, for at least 20 years, for at least 30 years, for at least 40 years). Alternatively, the energy harvesting material or a system comprising one or more, preferably a plurality of, energy harvesting materials, generates a sufficient amount of electrical energy to power a rechargeable battery that operates the device over the lifespan of the device (e.g. for at least 10 years or beyond 10 years, such as for at least 15 years, for at least 20 years, for at least 30 years, for at least 40 years).

The piezoelectric elements are located in and/or on the substrate in suitable orientation and in a sufficient amount to generate at least a few microJ to a few mJ of energy, depending on the mechanical stress provided by the underlying body part or second device to which the mechanical energy harvester is applied.

In some embodiments, the energy harvesting material or a system comprising one or more, preferably a plurality of, energy harvesting materials, generates at least approximately 3.5 V, preferably at least 3.7 V, more preferably 3.8V.

For example, for a stack of $n_{MEH}$ PZT MEHs thin, spin-cast layers of silicone layer in between as adhesives and strain isolating layers. The silicone, which is much more compliant (Young's modulus 60 KPa) than the PI (Young's modulus 2.5 GPa), does not significantly alter the modes of deformation of the PZT MEHs. As a result, for a stack of $m_{MEH}$ PZT MEHs, for $\Delta L_{max}$=10 mm, multilayer stacks with $n_{MEH}$=3 and 5, in vitro experiments described in the Examples showed peak voltages of 5.8 V and 8.1V, respectively. Both values are higher than that (3.7 V) for a single layer device. The time-averaged power density increases with $n_{MEH}$, and can reach as large as 1.2 $\mu$W/cm$^2$ for $n_{MEH}$=5, which is sufficient to operate a cardiac pacemaker or another device.

ii. Orientation

Orientation also impacts the efficiency of the system or device containing the energy harvesting material(s). For example, for a system containing one or more energy harvesting materials with PZT ribbons, bending in the longitudinal direction ($x_1$ direction) relative to the orientation of the PZT ribbons provides the highest efficiency.

As described in the Examples, to examine the dependence on orientation on the heart, measurements involved the longitudinal direction of PZT ribbons along 0°, 45° and 90° directions with respect to the apex of the heart. The 0° and 45° directions produced greater voltages than those for 90°.

iii. Energy Storage

The energy harvesting material or a system comprising one or more, preferably a plurality of, energy harvesting materials, preferably generates a sufficient amount of electrical energy to power a rechargeable battery that operates the device over the lifespan of the device (e.g. for at least 10 years or beyond 10 years, such as for at least 15 years, for at least 20 years, for at least 30 years, for at least 40 years).

iv. Overall Flexibility

The mechanical energy harvesting material is configured to reduce the strain for the piezoelectric materials. The computed bending stiffness (per unit width) for the energy harvesting material or a system containing one or more energy harvesting materials is sufficient to conform to a surface with curves or undulations, such as the surface of a human heart. Preferably the computed bending stiffness (per unit width) is approximately 0.22 Nmm for regions coincident with the piezoelectric materials, and preferably approximately 0.10 Nmm for regions without the piezoelectric materials, respectively. For a bending radius of 2.5 cm, the maximum strain in the piezoelectric materials typically ranges from 0.09798% to 0.0998%, preferably up to 0.1%.

v. Dimensions

The mechanical energy harvesting (MEH) material can have any suitable dimensions for powering a particular device. The MEH material is configured to be attached to a surface, such as the surface of a contractile or mobile organ, such as the heart, diaphragm, or lung, a lumen of a tubular organ or vessel in the body, or outside of a patient's body, e.g., on the sole of the foot, over a joint, or even to the surface of a device, where the surface moves or is in contact with another substance that moves (e.g. flows) over the surface.

For the heart, the MEH material typically covers the surface area of a ventricle, e.g. 5-25 cm×5-25 cm, or envelopes the entire organ as a sock or enveloping device akin to the pericardium. Similarly for the lung, a patch may be configured with dimensions ranging from approximately 2 cm$^2$ to approximately 625 cm$^2$. Further the MEH material may have a shape and configuration suitable for enveloping the lung, acting like an artificial pleura, covering the entire surface of the lung.

For an endoluminal construct in a blood vessel, a stent-like construct may be fashioned ranging in diameter from 2 mm to 30 mm with lengths ranging from 5 to 250 mm.

B. Flexible Substrate

The flexible substrate serves as a base for the mechanical energy harvesting material. The flexible substrate is able to establish conformal contact with large areas (up to several m$^2$) of smooth surfaces, flat surfaces, rough surfaces, particularly surfaces having roughness amplitudes up to about 1 micron, and contoured surfaces, preferably surfaces having radii of curvature up to about 25 microns. For example, use of a low modulus polymer allows conformal contact to be established between the contact surface(s) and large areas of substrate surface using relatively low pressures (about 0.1 kN/m$^2$ to about 10 kN/m$^2$) applied to the external surface of the flexible material.

Representative flexible substrates can be natural elastomers, thermoplastic elastomers, styrenic materials, olefenic materials, polyolefin, polyurethane thermoplastic elastomers, polyamides, synthetic rubbers, silicon-based organic polymers including polydimethylsiloxane (PDMS), polybutadiene, polyisobutylene, poly(styrene-butadiene-styrene), polyurethanes, polychloroprene, silicones, Synthetic polyisoprene, Polybutadiene, Chloropene rubber, polychloropene, Neoprene, Baypren, Butyl rubber (copolymer of isobutylene and isoprene, IIR), Halogenated butyl rubbers (chloro butyl rubber: CIIR; bromo butyl rubber: BIIR), Styrene-butadiene Rubber (copolymer of styrene and butadiene, SBR), Nitrile rubber (copolymer of butadiene and acrylonitrile, NBR), Hydrogenated Nitrile Rubbers (HNBR) Therban and Zetpol, EPM (ethylene propylene rubber, a copolymer of ethylene and propylene) and EPDM Rubber (ethylene propylene diene rubber, a terpolymer of ethylene, propylene and a diene-component), Epichlorohydrin rubber Polyacrylic rubber, Silicone rubber, Flurosilieone Rubber, Fluorosilicone Rubber, Fluroelastomers Viton, Tecnoflon, Fluorel, Aflas and Dai-El, Perfluoroelastomers Tecnoflon PFR, Kalrez, Chemraz, Perlast, Polyether block amides, Chlorosulfonated polyethylene, Hypalon, Ethylene-vinyl acetate, and combinations thereof.

Suitable materials for the flexible substrate are preferably biocompatible. Suitable materials include, but are not limited to elastomers and other flexible polymers, woven or stretchable materials, flexible interlinked rings (e.g. chain mail) or mesh materials. Exemplary materials for the flexible substrate include but are not limited to, polyurethanes, silicon rubber, polyethers, polyesters, co-polymers of polyether urethanes, polyester urethanes, polysulfones, polybutadiene-styrene, elastomers, hydrogels formed from copolymers of polyethylene glycol and polylactide, polyglycolide or copolymers of polylactide-co-glycolide, or materials such as those described in *Adv. Mat.*, vol. 25, issue 8, Article first published online: 12 Dec. 2012.

"Elastomer" refers to a polymeric material that can be stretched or deformed and return to its original shape without substantial permanent deformation. Elastomers commonly undergo substantially elastic deformations. Exemplary elastomers may contain polymers, copolymers, composite materials or mixtures of polymers and copolymers. "Elastomeric layer" generally refers to a layer that contains at least one elastomer. Elastomeric layers may also include dopants and other non-elastomeric materials. Elastomers can also provide elastomeric stamps used to form the energy harvesting.

"Elastomeric stamp" or "elastomeric transfer device" are used interchangeably and refer to an elastomeric material having a surface that can receive as well as transfer a feature. Exemplary elastomeric transfer devices include stamps, molds and masks. The transfer device affects and/or facilitates feature transfer from a donor material to a receiver material.

Suitable elastomers include, but are not limited to, natural elastomers, such as latex, thermoplastic elastomers, styrenic materials, olefenic materials, polyolefin, polyurethane thermoplastic elastomers, polyamides, synthetic rubbers, silicon-based organic polymers including polydimethylsiloxane (PDMS), polybutadiene, polyisobutylene, poly(styrene-butadiene-styrene), polyurethanes, polychloroprene and silicones.

The flexible material may be formed from a polymer, such as an elastomer, preferably with a low modulus. In a preferred embodiment, Young's modulus for an elastomer is less than 2 GPa, preferably less than 1 GPa. See for example, Mechanical Behavior of Materials, 2d ed., Mark Myers and Krishan Chawla, Cambridge Press, 2009, Chapter 2, Table 2.1 reproduced below.

TABLE 1

| Young's Modulus for Polymers | |
|---|---|
| Material | E (GPa) |
| Phenolformaldehyde | 8 |
| Melamines | 6-7 |
| Polymides | 3-5 |
| Polyesters | 1.3-4.5 |
| Acrylics | 1.6-3.4 |
| Nylon | 2-4.5 |
| PMMA | 3.4 |
| Polystyrene | 3-3.4 |
| Polycarbonate | 2.1 |
| Epoxies | 2.1-5.5 |
| Polypropylene | 1.2-1.7 |
| Polyethylene, high-density | 0.15-0.24 |
| Foamed polyurethane | 0.01-0.06 |
| Polyethylene, low-density | 0.15-0.24 |
| Rubbers | 0.01-0.1 |
| PVC (unplasticized) | 2.4-3.0 |
| Foamed polymers | 0.001-0.1 |

Figure 14:
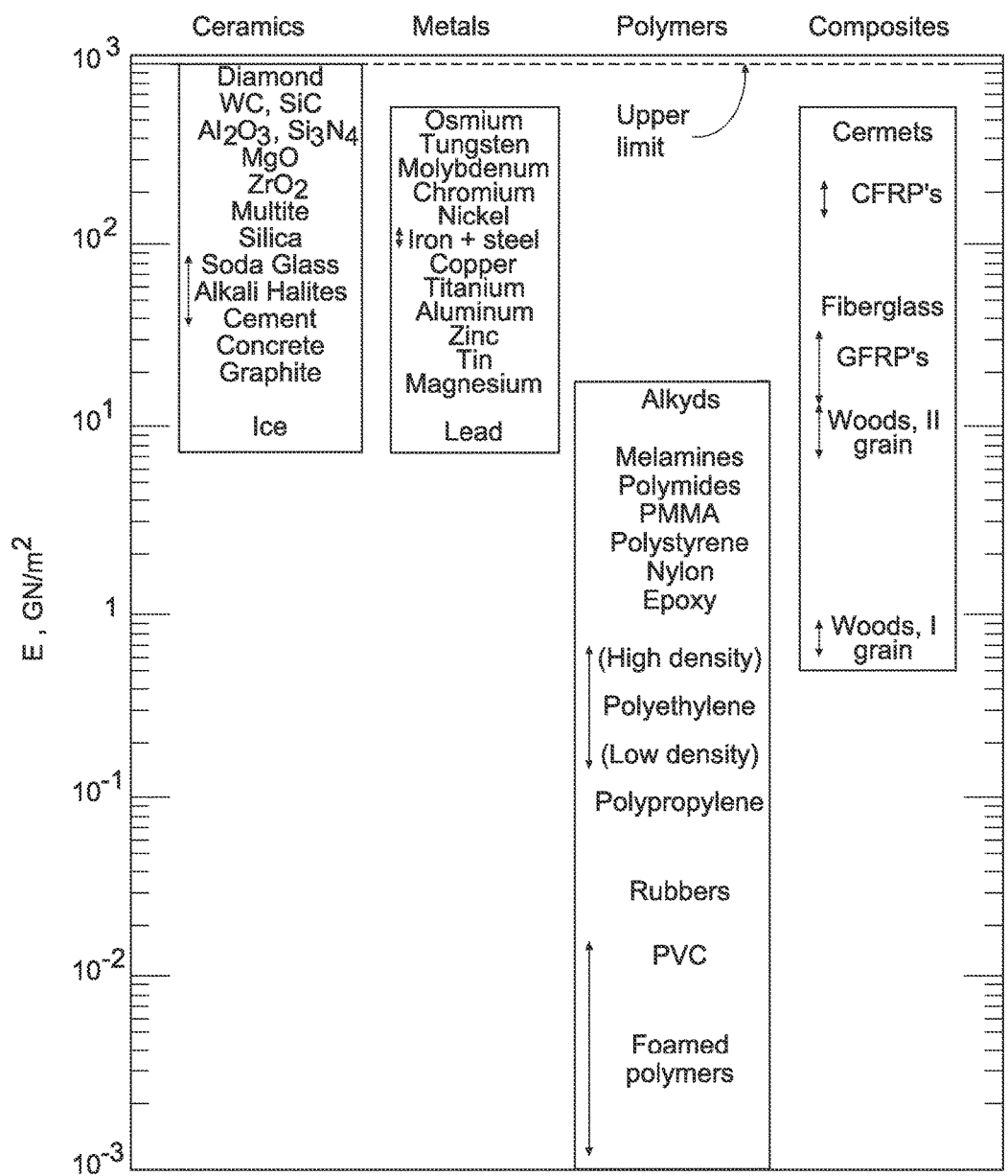
FIG. 14 is a bar chart of data for Young's moduli for the indicated materials (Mechanical Properties of Materials, 2ed., Mark Myers and Krishan Chawla, Cambridge Press, 2009 adapted from M. F. Ashby and D. R. H. Jones, Engineering Materials (Oxford:Pergamon Press, 1980), p. 32). The units of Young's moduli are shown in E which is equivalent to GPa.

FIG. 14 shows the Young's modulus for various materials from very stiff materials such as diamonds to very elastic materials such as foamed polymers.

"Low modulus" or "low Young's modulus" refers to materials having a Young's modulus of about 0.01 to 5.0 GPa, preferably about 0.1 to 2.0 GPa, more preferably about 0.1 to 1.0 GPa.

An exemplary suitable elastomer with a low modulus contains a PDMS layer having a thickness greater than or equal to about 5 microns establishes reproducible conformal contact over substrate surface areas as large as 250 cm$^2$ upon application of external pressures less than or equal to about 100 N/m². The Young;s modulus for PDMS is less than 1.0 GPa and typically ranges from 0.380 to 0.870 GPa.

U.S. Pat. No. 8,552,299 to Rogers, et al. discloses flexible materials for use in electronic devices and methods of making the devices. U.S. Publication No. 2008/0055581 to J. A. Rogers & E. Menard discloses methods for pattern generation by ink lithography, which is useful to flexible electronics. Kim, et al., "Epidermal Electronics," *Science* 333, 838-843 (2011) discloses flexible materials for use in electronic devices that are suitable for application to the surface of skin. The disclosures of these references are incorporated herein by reference.

Rubber has a low Young's modulus of 0.01-0.1 GPa. Polypropylene has a Young's modulus of 1.5-2 GPa. Oak Wood has a Young's modulus of 11 GPa. Human cortical bone has a Young's modulus of 14 GPa. Aluminum has a Young's modulus of 69 GPa. Steel has a Young's modulus of 200 GPa. Thus, a medium range for Young's modulus would be greater than 4.0 to 15.0 GPa. A high range would be greater than 15.0 GPa to a least 200 GPa.

A high Young's modulus is larger than a low Young's modulus, and is greater than 10 GPa preferably about 10 times larger than the low Young's modulus material in a mechanical energy harvesting material for some applications, more preferably about 100 times larger than the low Young's modulus material in a mechanical energy harvesting material for other applications and even more preferably about 1000 times larger than the low Young's modulus material in a mechanical energy harvesting material for yet other applications. Exemplary materials with a high modulus, i.e., greater than 15 GPa, are shown in FIG. 14.

"Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire layer of material.

Optionally, the MEH contains a composite structure (heterogeneous integration) of low and high modulus materials.

C. High Modulus Material

Preferably, the energy harvesting material contains a second polymer layer that is a high modulus material that is in contact with the piezoelectric elements. The high modulus material shifts the neutral mechanical plane (NMP) out of the middle point within the active piezoelectric material. See Gere & Timoshenko, *Mechanics of Materials: Solutions Manual* (Nelson Thornes) (2003).

The use of a high modulus second polymer layer in the devices also provides devices having a net flexural rigidity large enough to minimize distortions of the relief pattern which may occur upon formation of conformal contact between the contact surface(s) and a substrate surface. Incorporation of a high modulus second polymer layer into patterning devices minimizes distortions of the relief pattern in planes parallel to a plane containing the contact surface, such as distortions characterized by the collapse of narrow relief features of patterns having high aspect ratios. Additionally, incorporation of a high modulus second polymer layer minimizes distortions of the relief pattern in planes which intersect a plane containing the contact surface, such as distortions characterized by sagging of recessed regions of a relief pattern. This reduction in relief pattern distortion provided by incorporation of a high modulus second polymer layer allows patterns of small structures comprising well defined features having physical dimensions as small as 50 nanometers to be fabricated using patterning devices and methods, such as those described in U.S. Publication No. 2008/0055581.

D. Piezoelectric materials

The energy harvesting materials include one or more power generation elements capable of generating sufficient electrical energy to power one or more integrated electronic components. The piezoelectric materials can convert the motion of the body, tissue, organ or organ component or of a device or machine into electrical current.

Many materials, both natural and synthetic, exhibit piezoelectricity. Naturally occurring crystals that exhibit piezoelectricity include, but are not limited to, Berlinite ($AlPO_4$), Sucrose (table sugar), Quartz, Rochelle salt, Topaz, and Tourmaline-group minerals. Synthetic crystals that exhibit piezoelectricity include, but are not limited to, Gallium orthophosphate ($GaPO_4$) and Langasite ($La_3Ga_5SiO_{14}$). Synthetic ceramics that exhibit piezoelectricity include, but are not limited to, Barium titanate ($BaTiO_3$), Lead titanate ($PbTiO_3$), Lead zirconate titanate ($Pb[Zr_xTi_{1-x}]O_3$, $0 \leq x \leq 1$) (commonly referred to as PZT), Potassium niobate ($KNbO_3$), Lithium niobate ($LiNbO_3$), Lithium tantalate ($LiTaO_3$), Sodium tungstate ($Na_2WO_3$), Zinc oxide (ZnO), $Ba_2NaNb_5O_5$, and $Pb_2KNb_5O_{15}$. Lead-free piezoceramics that exhibit piezoelectricity include, but are not limited to, Sodium potassium niobate (($K,Na)NbO_3$) (also known as NKN), Bismuth ferrite ($BiFeO_3$), Sodium niobate ($NaNbO_3$), Bismuth titanate ($Bi_4Ti_3O_{12}$), and Sodium bismuth titanate ($Na_{0.5}Bi_{0.5}TiO_3$) See (Maeder and Setter, *J Electroceramics*, 13:385-392, (2004)). Additional materials include polyvinylidene fluoride (PVDF) and poly[(vinylidenefluoride-co-trifluoroethylene] [P(VDF-TrFE)].

Suitable piezoelectric materials include, but are not limited to, piezoelectric crystals such as gallium phosphate, quartz, and tourmaline; or thin films or nanoparticles made from piezoelectric ceramics, such as barium titanate, lead zirconate, lead titanate, and/or lead zirconate titanate (PZT); or organic piezoelectric materials such as polyvinylidene fluoride.

The piezoelectric material is positioned within the flexible material such that when it is in use, the motion of the body, tissue, organ, organ component or fluid results in the generation of an electric current. For example, the contraction of the muscular tissue causes an impact, deformation, vibration, or bending of the piezoelectric element, which generates an electric current. In some embodiments the electric current is provided directly to one or more integrated electronic components. Optionally the piezoelectric material may be used to charge a battery or a capacitor.

1. PZT

In the preferred embodiment, the piezoelectric material is PZT. Lead zirconium titanate is an intermetallic inorganic compound with the chemical formula $Pb[Zr_xTi_{1-x}]O_3$, $0 \leq x \leq 1$) (commonly referred to as PZT). PZT is a ceramic perovskite material that shows a marked piezoelectric effect, with practical applications in the area of electroceramics. It is a white solid that is insoluble in all solvents.

PZT is one of the most widely used ferroelectric materials, due to its excellent piezoelectric and ferroelectric properties. Many classes of sensors, actuators, and memory elements for use in diverse sectors of industry, ranging from aerospace, automotive, to medicine and microelectronics, rely on PZT. See, e.g. Damjanovic, D., "Ferroelectric, Dielectric and Piezoelectric Properties of Ferroelectric Thin Films and Ceramics," *Rep. Prog. Phys.*, 61: 1267-1324 (199); Polla & Francis, "Processing and Characterization of Piezoelectric Materials and Integration into Microelectromechanical Systems", *Annu. Rev. Mater. Sci.,* 28:563-597 (1998); Muralt, P., "Piezoelectric Thin Films for MEMS", *Integr. Ferroelectr.,* 17: 297-307 (1997); Choi, et al., "Ferroelectric and Piezoelectric Properties of Highly Oriented Pb(Zr,Ti)$O_3$ Film Grown on Pt/Ti/Si$O_2$/Si Substrate Using Conductive Lanthanum Nickel Nitrate Buffer Layer", *J. Mater. Res.,* 20: 726-733 (2005). The dielectric constant of PZT can range from 300 to 3850 depending upon orientation and doping.

PZT is transversely isotropic with the polarization direction x3 normal to the surface.

2. Shape of Piezoelectric Materials

The piezoelectric materials may have any suitable shape and size. Typically, the piezoelectric materials range in size from about 200 nm to several mm (e.g. up to 10 mm). Piezoelectric materials may be in the shape of a ribbon, with thickness of 500 nm and an area of 100 µm×2.02 mm. Alternatively the piezoelectric materials may be in the shape of shorter structures, such as those having dimensions of thickness ranging from approximately 100 nm to 400 nm, width from approximately 20 nm to 90 nm, and length from approximately 20 nm to 1 mm.

3. Arrangement of Piezoelectric Elements in the Energy Harvesting Material

The energy harvesting material contains from approximately 85% to approximately 15% piezoelectric material (based on the surface area of the energy harvesting material).

The piezoelectric materials are configured in the energy harvesting material such that when the MEH material is applied to the surface in use, the piezoelectric materials align to match the underlying vectorial impact of the mechanical force. For example, in some embodiments, such as when the MEH material is applied to the surface of the heart, the piezoelectric materials may be aligned in a linear fashion.

III. Systems

One or more energy harvesting materials can be provided with other components to a form a system (also referred to herein as "mechanical energy harvester" or "MEH") that can be used to power one or more devices and/or provide energy to batteries.

The system can contain one or more energy harvesting materials. In some embodiments, the system contains a single MEH material. In other embodiments the system contains more than one MEH material, which can be the same or different (e.g. different piezoelectric materials, different flexible substrate materials, and/or different configurations). Preferably, the system contains more than one energy harvesting material, preferably in the form of stack.

Typically, the system also contains two electrodes.

Preferably, the system is enclosed in an encapsulation material. This is particularly preferred for systems that are used inside or attached to the body. Preferably the encapsulation material is a biocompatible material. Encapsulation of these systems with biocompatible materials isolates them from bodily fluids and tissue, thereby minimizing the risks of failure or rejection.

A. Optional Components

The energy generated by the MEH material can be captured directly by use, for example, of a chip-scale rechargeable battery (EnerChip CBC012, CYMBET Corporation) and a Schottky bridge rectifier (MB12S, CMM) co-integrated on the same flexible substrate with the MEHs.

Characterization to determine the voltage that can be created and optionally stored using the MEH described herein can be performed using the types of setups, such as described in the Examples.

A mechanical bending stage can be used to test MEH and systems thereof. An exemplary mechanical bending stage system can include a high precision linear stage (such as TS100-150; Aerotech, Inc.; USA), equipped with precision ground ball screw, noncontact rotary encoder with 1000 line/rev, and brushless servomotor to achieve a motion with an accuracy of ±0.5 µm and a bidirectional repeatability of ±0.3 µm over 150 mm stage motion range. The stage can achieve velocities up to 100 mm/sec with maximum side load of 100 N in horizontal configuration. The stage motion can be controlled with a Soloist single axis PWM digital controller (SOLOISTCP20; Aerotech, Inc.; USA) and USB interface. Additionally, two U-Form Vise grip (TH240k, Grip Engineering Thilmler GmbH; Germany) can be attached to the stage. Pyramid shape jaws (TH240k-BP, Grip Engineering Thümler GmbH; Germany) can be attached to the vices to achieve maximum tensile gripping force of 2.5 kN of a specimen during testing. A LabVIEW (National Instruments Corporation; USA) based program may be used to control the stage to perform the test cycle.

Figure 3A:
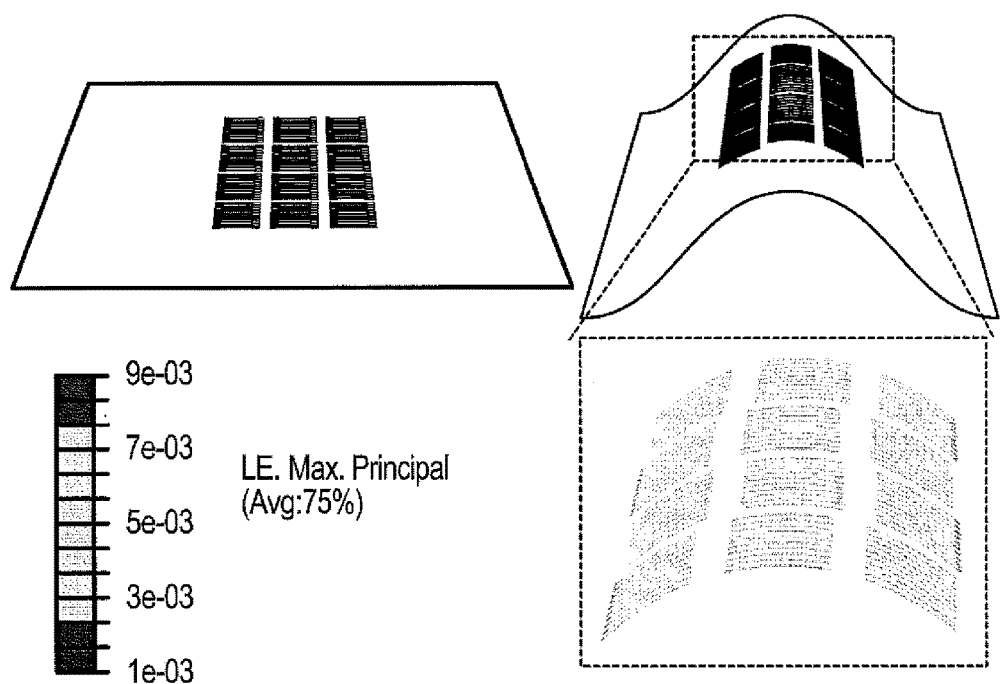
FIGS. 3A-3G.
Figure 3B:
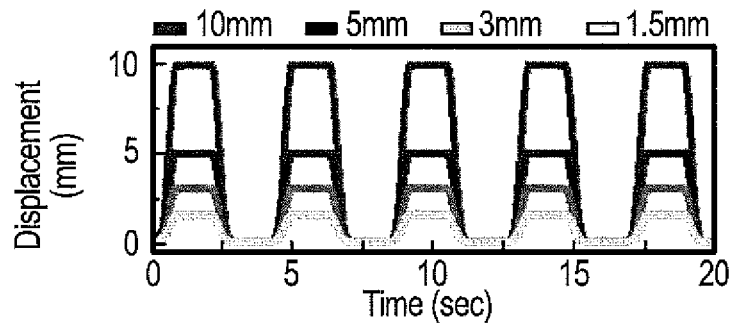
Figure 3C:
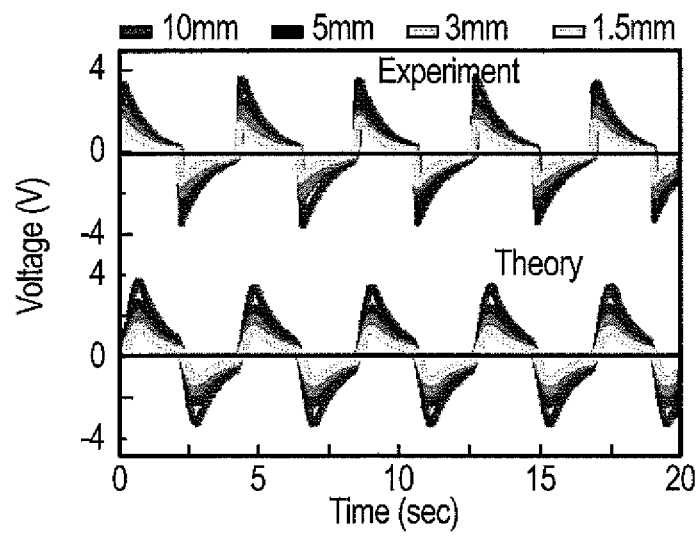
Figure 3D:
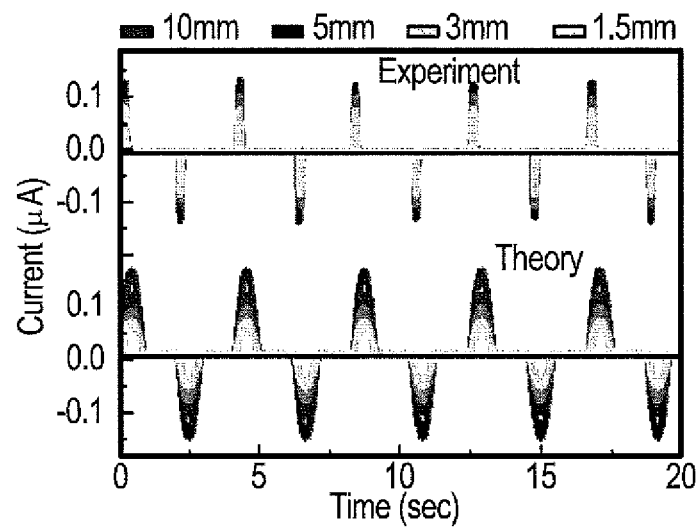
Figure 3E:
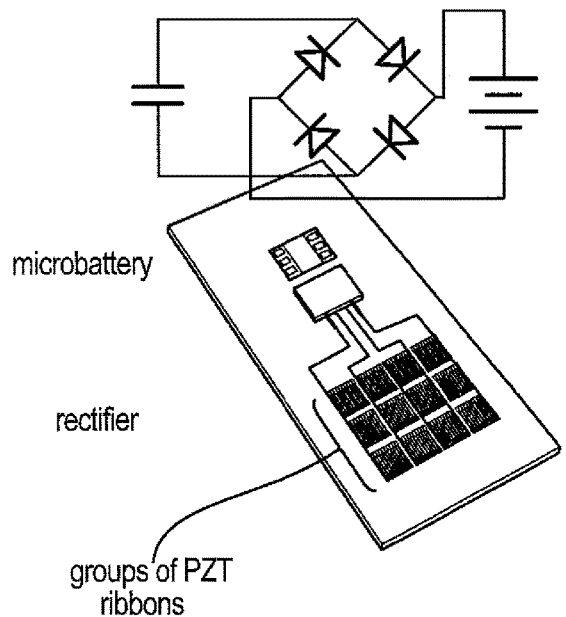
Figure 3F:
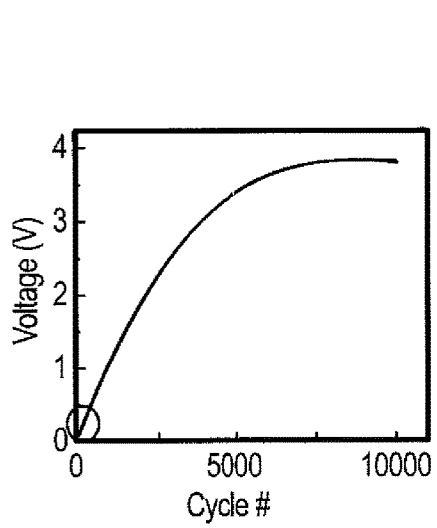
Figure 3G:
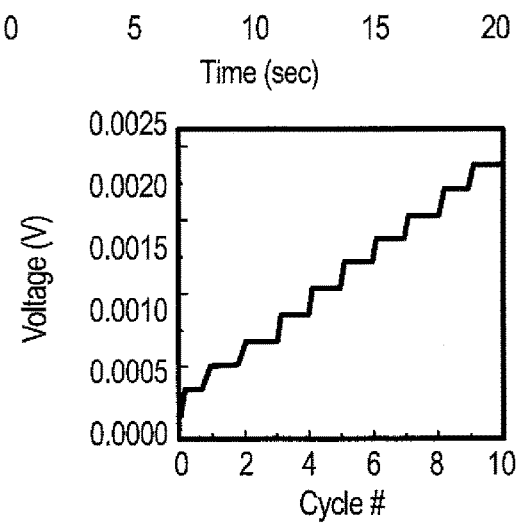

FIGS. 3F and 3G show an exemplary MEH device and the output voltage of the battery measured in such a case. The results showed stepwise increases in the stored energy with each cycle of bending and unbending. As the process continued, the voltage of the battery saturated at a value (~3.8 V) characteristic of the battery specification.

1. Rectifiers

Preferably the system contains a rectifier to convert alternating current (AC) to direct current (DC). Any suitable rectifier may be utilized. For example, a preferred rectifier is a Schottky bridge rectifier (such as MB12S, CMM).

Preferably the rectifier is integrated with the piezoelectric materials on the flexible substrate.

2. Filters

One or more filters capable of selectively filtering one frequency or a range of frequencies out of a mix of different frequencies in a circuit may be included in the device or system. One or more filters may be included after a rectifier in the circuit to smooth the output and produce a steady current.

3. Batteries or Microbatteries

The system optionally includes one or more batteries or microbatteries. The batteries or microbatteries are preferably cointegrated on the flexible subtrace with the piezoelectric elements.

In a preferred embodiment, the energy produced by the device can be captured directly by use of a chip-scale rechargeable battery (such as EnerChip CBC012, CYMBET Corporation) and a rectifier, such as a Schottky bridge rectifier (MB12S, CMM), which are co-integrated on the same flexible substrate material with the piezoelectric materials.

B. Theory

Although not required and without wishing to be bound by theory, a possible explanation for the flexible energy harvesting materials and systems containing these materials and some of the related calculations are provided below.

For illustration purposes, this section refers to the materials and devices described in the Examples section. However, one of skill in the art will appreciate that these materials and devices could be modified to have alternative configurations, alternative piezoelectric materials, alternative high modulus materials, and/or alternative flexible substrate materials.

1. Mechanics Analysis

Figure 2A:
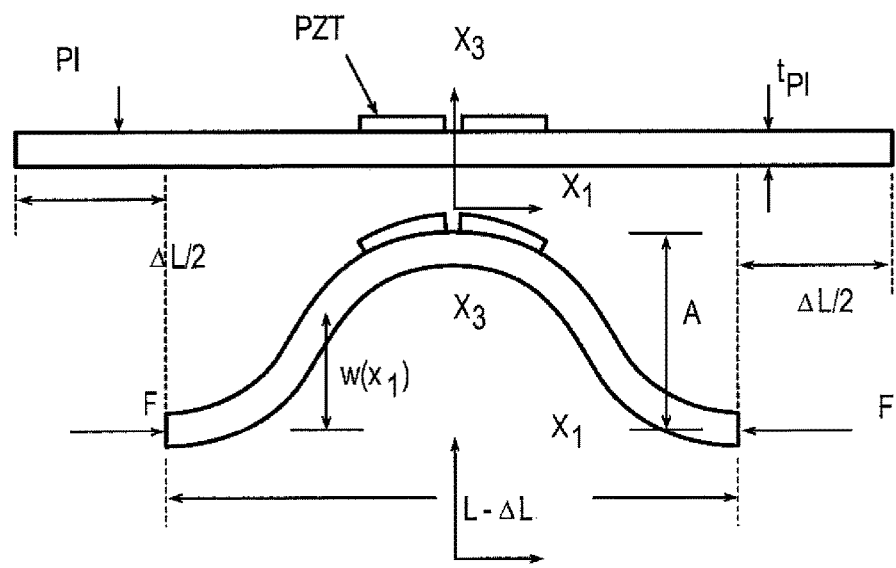
FIGS. 2A-2C are exemplary device layouts and labeled with variable names and physical parameters used in calculations described herein.

For the out-of-plane displacement $w=A[1+\cos(2\pi x_1/L)]/2$ shown in FIG. 2A for plane-strain analysis ($\varepsilon_{22}=0$), the bending energy in polyimide (PI) is related to the curvature w" by $(\overline{EI}_{PI}/2)\int(w")^2 ds$, where the integration is over the PI length, and $\overline{EI}_{PI}=(\overline{E}_{PI}t_{PI}^3)/12$, $\overline{E}_{PI}$ and $t_{PI}$ are the plane-strain bending stiffness, plane-strain modulus, and thickness of PI, respectively. The membrane energy can be obtained following the same approach of Song J, et al., "Mechanics of noncoplanar mesh design for stretchable electronics circuits," *Journal of Applied Physics*, 105:123516 (2009). Minimization of the total energy (sum of bending and membrane energies) gives the amplitude A as $$A = \frac{2}{\pi}\sqrt{L \cdot \Delta L - \frac{\pi^2 t_{kapton}^2}{3}} \approx \frac{2}{\pi}\sqrt{L \cdot \Delta L}, \quad (S1)$$

where the last approximation holds when the compression of PI $\Delta L$ is much larger than its critical value $\pi^2 t_{PI}^2/(3L)$ to initiate buckling. For example, for a 75 μm—thick and 2.5 cm-long PI, $\pi^2 t_{PI}^2/(3L) \sim 0.74$ μm is negligible as compared to compression $\Delta L = 1.5 \sim 10$ mm in the experiments described in the Examples.

Figure 2B:
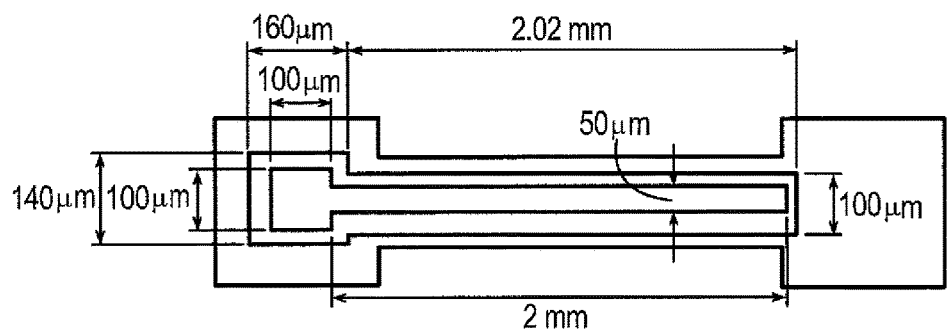
Figure 2C:
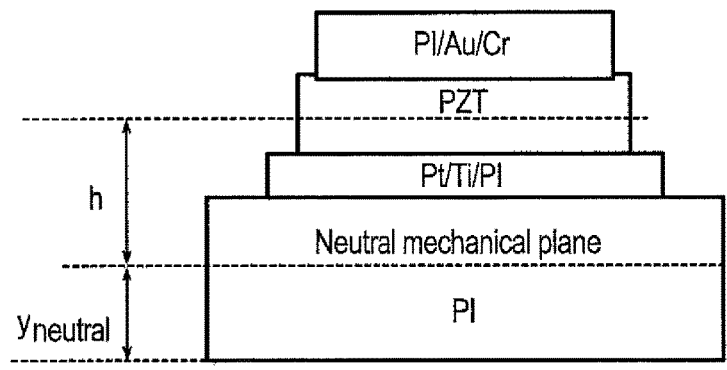

The bending moment M in PI is related to the curvature w" by $M=\overline{EI}_{PI}w"$. For the part of PI covered by the PZT ribbons (FIG. 2B), the local curvature is reduced to $M/\overline{EI}_{comp}$ due to the additional bending stiffness of PZT ribbons, where $$\overline{EI}_{comp} = \sum_{i=1}^{n} \overline{E}_i t_i \left[ t_i^2/3 + \left(\sum_{j=1}^{i} t_j - y_{neutral}\right)\left(\sum_{j=1}^{i} t_j - y_{neutral} - t_i\right) \right]$$

is the effective bending stiffness of multi-layer structure (FIG. 3B) with PI as the 1$^{st}$ layer (i=1) and the summation over all n layers, $\overline{E}_i$ and $t_i$ are the plane-strain modulus and thickness of the i$^{th}$ layer, respectively, and $$y_{neutral} = \left[\sum_{i=1}^{n} \overline{E}_i t_i \left(2\sum_{j=1}^{i} t_j - t_i\right)\right] / \left(2\sum_{i=1}^{n} \overline{E}_i t_i\right)$$

is the distance from the neutral mechanical plane to the bottom of 1$^{st}$ (PI) layer. The membrane strain in PZT is the axial strain at the center of PZT ribbons, and is given by $\varepsilon_m = (\overline{EI}_{PI}/\overline{EI}_{comp})w"h$, (S2)

where h is the distance from the center of each PZT ribbon to the neutral mechanical plane of the cross section as shown in FIG. 2B. For the length of PZT ribbons much smaller than that of the PI, w" is evaluated at the center $x_1=0$ of PZT ribbons as $w"=4\pi\sqrt{\Delta L/L}/L$, which gives the membrane strain as shown in Eq. (1) (discussed in Examples).

For the structure shown in FIG. 2B, in Eq. 1, $\overline{E}_1=2.83$ GPa and $t_1=75$ μm for PI, $\overline{E}_2=2.83$ GPa and $t_2=1.2$ μm for the PI layer, $\overline{E}_3$ 0.129 GPa and $t_3=20$ nm for the Ti layer, $\overline{E}_4=196$ GPa and $t_4=0.3$ μm for the Pt layer, $\overline{E}_5=69.2$ GPa and $t_5=0.5$ μm for the PZT layer, $\overline{E}_6=292$ GPa and $t_6=10$ nm for the Cr layer, $\overline{E}_7=96.7$ MPa and $t_7=0.2$ μm for the Au layer, and $\overline{E}_8=2.83$ GPa and $t_8=1.2$ μm for the PI layer; these give $\overline{EI}_{PI}/\overline{EI}_{comp}=0.45$, $y_{neutral}=52.0$ μm and $h=(t_1+t_2+t_3+t_4+t_5/2)-y_{neutral}=24.7$ μm.

2. Piezoelectric analysis

The constitutive model of piezoelectric materials gives the relations among the stress $\sigma_{ij}$, strain $\varepsilon_{ij}$, electrical field $E_i$ and electrical displacement $D_i$ as $$\begin{Bmatrix} \sigma_{11} \\ \sigma_{22} \\ \sigma_{33} \\ \sigma_{23} \\ \sigma_{31} \\ \sigma_{12} \end{Bmatrix} = \begin{pmatrix} c_{11} & c_{12} & c_{13} & 0 & 0 & 0 \\ c_{12} & c_{11} & c_{13} & 0 & 0 & 0 \\ c_{13} & c_{13} & c_{33} & 0 & 0 & 0 \\ 0 & 0 & 0 & c_{44} & 0 & 0 \\ 0 & 0 & 0 & 0 & c_{44} & 0 \\ 0 & 0 & 0 & 0 & 0 & (c_{11}-c_{12})/2 \end{pmatrix} \begin{Bmatrix} \varepsilon_{11} \\ \varepsilon_{22} \\ \varepsilon_{33} \\ 2\varepsilon_{23} \\ 2\varepsilon_{31} \\ 2\varepsilon_{12} \end{Bmatrix} - \quad (S3)$$

$$\begin{pmatrix} 0 & 0 & e_{31} \\ 0 & 0 & e_{31} \\ 0 & 0 & e_{33} \\ 0 & e_{15} & 0 \\ e_{15} & 0 & 0 \\ 0 & 0 & 0 \end{pmatrix} \begin{Bmatrix} E_1 \\ E_2 \\ E_3 \end{Bmatrix},$$

$$\begin{Bmatrix} D_1 \\ D_2 \\ D_3 \end{Bmatrix} = \begin{pmatrix} 0 & 0 & 0 & 0 & e_{15} & 0 \\ 0 & 0 & 0 & e_{15} & 0 & 0 \\ e_{31} & e_{31} & e_{33} & 0 & 0 & 0 \end{pmatrix} \begin{Bmatrix} \varepsilon_{11} \\ \varepsilon_{22} \\ \varepsilon_{33} \\ 2\varepsilon_{23} \\ 2\varepsilon_{31} \\ 2\varepsilon_{12} \end{Bmatrix} + \quad (S4)$$

$$\begin{pmatrix} k_{11} & 0 & 0 \\ 0 & k_{22} & 0 \\ 0 & 0 & k_{33} \end{pmatrix} \begin{Bmatrix} E_1 \\ E_2 \\ E_3 \end{Bmatrix}.$$

The plane-strain condition $\varepsilon_{22}=0$ of PZT ribbons, together with $\sigma_{33}=0$ from the traction free on the top surface of the structure, gives $D_3=\overline{e}\varepsilon_{11}+\overline{k}E_3$, where $\overline{e}=e_{31}-(c_{13}/c_{33})e_{33}$ and $\overline{k}=k_{33}+(e_{33}^2/c_{33})$ are the effective piezoelectric constants. The electrical displacement can be further obtained as $$D_3 = \overline{e}\varepsilon_m + \frac{\overline{k}V}{Nt_{PZT}} \quad (S5)$$

from the charge equation $dD_3/dx_3=0$ and the relation $E_3=-\partial\phi/\partial x_3$ between the electrical field and electrical potential, together with the boundary condition that the voltage difference between the bottom and top of PZT is V/N, where V is total voltage between the two ends of the N groups of PZT ribbons in series, and $t_{PZT}$ is the thickness of PZT ribbons. Eq. (S5) shows that the electrical displacement is linear with the membrane strain of PZT ribbons, and is independent of the bending strain. Therefore the bending strain does not contribute to the voltage and current output of the MEH given in the following.

a. Current

The voltage V across the two ends of the N groups of PZT ribbons in series is zero after the PZT ribbons were connected to an ampere meter. The electrical displacement in Eq. (S5) then becomes $D_3=\overline{e}\varepsilon_m$, where $\varepsilon_m$ is given in Eq. (1).

Its rate gives the current $I=-A_{PZT}\dot{D}_3$, or equivalently Eq. (2), where $A_{PZT}=m(w_{PZT,1}l_{PZT,2}+w_{PZT,2}l_{PZT,2})$ is total area of PZT ribbons in each group; m=10 is the number of PZT ribbons in each group, $w_{PZT,1}$=100 μm, $w_{PZT,2}$=140 μm, $l_{PZT,1}$=2 mm and $l_{PZT,2}$=160 μm are the widths and lengths of the two rectangular parts of each PZT ribbon, respectively (FIG. 2B).

b. Voltage

For voltage measurement, the voltage V in Eq. (S5) across the two ends of the N groups of PZT ribbons in series is no longer zero after the PZT ribbons are connected to a voltmeter. The rate of the displacement in Eq. (S5) gives the current $I=-A_{PZT}\{\bar{e}\dot{\varepsilon}_m+[\bar{k}/(Nt_3)]\dot{V}\}$, which, together with the Ohm's law gives Eq. (4) (discussed in the Examples).

3. Rectifier

For measurements where the PZT ribbons in series were connected with the rectifier, such as illustrated in FIG. 3E, the resistance across the PZT groups is no longer zero because of the resistance of the rectifier $R_{rectifier}$. Instead it is the same as the voltage measurement shown FIG. 3B except that the resistance of the voltmeter R is replaced by $R_{rectifier}$. After this replacement Eq. (5) (see Examples) still holds, but is taken by its absolute value because of the rectifier. The current is then obtained from Ohm's law as $$I = \frac{1}{R_{rectifier}}\frac{(-\bar{e})Nt_{PZT}}{\bar{k}}e^{\frac{Nt_{PZT}}{A_{PZT}R_{rectifier}\bar{k}}t}\left|\int_0^t \frac{d\varepsilon_m}{dt}e^{\frac{Nt_{PZT}}{A_{PZT}R_{rectifier}\bar{k}}t}dt\right|. \quad (S6)$$

Figure 4A:
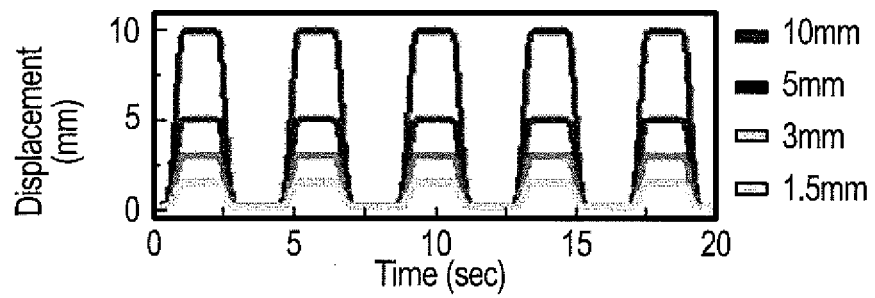
FIGS. 4A-4C contain three graphs depicting experimental and theoretical results for displacement ($\Delta L$, mm) (FIG. 4A), voltage (V) (FIG. 4B), and current ($\mu A$) (FIG. 4C) as a function of time (seconds) for cyclic bending of a PZT MEH with rectification.
Figure 4B:
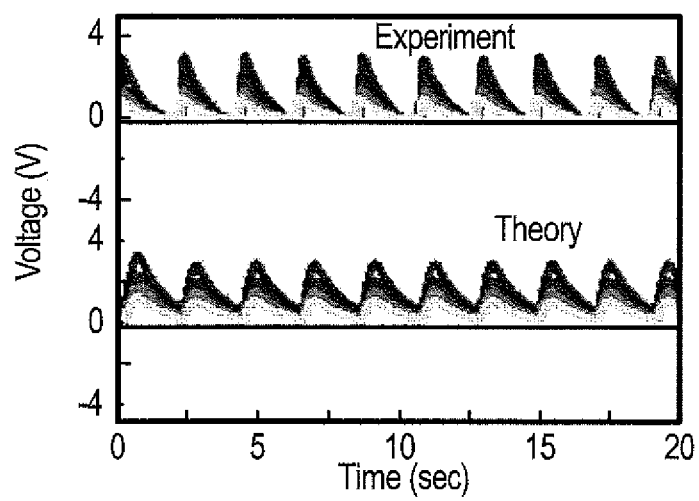
Figure 4C:
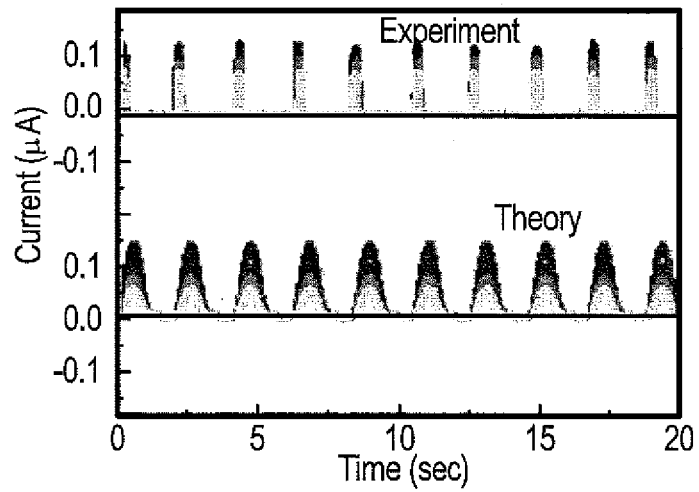

For the voltage measurement with the rectifier (see FIG. 4), the resistance R is replaced by $R+R_{rectifier}$. After this replacement Eq. (5) still holds for the voltmeter and rectifier in series, and the voltage on the voltmeter is then obtained by multiplying the factor $R/(R+R_{rectifier})$ of the absolute value of Eq. (5) as $$V = \frac{R}{R+R_{rectifier}}\frac{(-\bar{e})Nt_{PZT}}{\bar{k}} \quad (S7)$$
$$e^{\frac{Nt_{PZT}}{A_{PZT}(R+R_{rectifier})\bar{k}}t}\left|\int_0^t \frac{d\varepsilon_m}{dt}e^{\frac{Nt_{PZT}}{A_{PZT}(R+R_{rectifier})\bar{k}}t}dt\right|.$$

4. Direction of Bending

The strain in PZT bent along $x_1$ and $x_2$ directions, respectively, for the axial compression of a variety of displacement values (e.g., ΔL=1.5, 3, 5 and 10 mm), can be observed. For the same axial compression ΔL, the strain in PZT bent along $x_1$ direction is generally larger than that along $x_2$ direction, and is therefore more effective for energy harvesting.

5. The Time-Averaged Power Density

The electrical energy output can be calculated by integrating the ratio of the square of the voltage V and the resistance R over total time $t_{total}$ as $$W = \int_0^{t_{total}} V^2/R\,dt. \quad (4)$$

The time-averaged power density is given by $P=W/(t_{total}NA_{PZT})$.

IV. Uses a. Biologics

A variety of different wearable, implantable biomedical devices rely on some form of battery power for operation. Implantable devices that can be modified to be powered by the energy harvesting materials and systems described herein include, but are not limited to heart rate monitors, pacemakers, implantable cardioverter defibrillators (ICDs), blood and fluid pumps, tissue and neural stimulators tissue sensors, monitors and actuators and drug delivery systems.

The energy harvesting materials and systems may be in contact with any surface that moves. It may be in contact with an ectoluminal surface or an endoluminal surface. They also may be implanted within a tissue, i.e. within an endomural space or domain.

The Examples indicate that the materials and systems disclosed herein are capable of powering implanted devices. The magnitude of power generation in this context is significant compared to prior art materials, which are unable to be used to power such devices. For example, state-of-the-art cardiac pacemaker devices offer cardiac activity sensing, adaptive pacing, and programmability, with average power consumption to values as low as 0.3 μW (Silveira F, et al., "*Low power analog CMOS for cardiac pacemakers: design and optimization in bulk and SOL technologies*" Kluwer Academic Publishers (2004); Ohm O J, et al., "Improvements in pacemaker energy consumption and functional capability: four decades of progress," *Pacing and Clinical Electrophysicology*, 20 (1): 2-9 (1997)).

The implantable devices can be connected to one or more energy harvesting materials and/or systems to provide power to an implantable medical device. In some embodiments, the device contains or is connected to one or more rechargeable batteries and the energy harvesting materials, and the energy harvesting materials are used as a back-up source of energy to the device. In these embodiments, the energy harvesting materials are in electrical communication with the rechargeable batteries to recharge the batteries when needed.

In other embodiments, the device contains or is connected to one or more rechargeable batteries and the energy harvesting materials and the energy harvesting materials are configured to serve as the primary source of energy to the device, with the batteries serving as a back up energy source. Preferably, the energy harvesting materials and/or systems are able to provide a sufficient amount of energy to power the device; in the absence of conventional batteries.

i. Ectoluminal

The material may be attached to an ectoluminal surface to power one or more devices implanted inside a patient's body or outside of the individual's body. Ectoluminal surfaces include an outer surface of an internal organ or vessel, organ component or tissue structure with motility or contraction, or outside an individual's body, such as on the arm, leg, foot, or other portion of the body. For example, the ectoluminal surface may be on the outer surface of the heart or lung; a muscle or muscle group, such as the quadriceps; a tendon, a ligament, the alimentary canal from the oropharynx to the anus, the ureter, the bladder, or other similar organ, organ component or tissue structure.

Typically, prior to delivery of the system containing one or more energy harvesting materials, the particular surface of the body with which the system will be in contact is imaged using suitable imaging techniques (e.g., ultrasound, doppler, magnetic resonance imaging (MRI), computed tomography (CT), optical imaging (fluorescence and bioluminescence), positron emission tomography (PET), or single photon emission computed tomography (SPECT), or combinations thereof) to image the motion of the vessel or relevant portion thereof. Then the one or more MEH materials or systems are attached to the surface of the vessel or portion thereof, such that the piezoelectric materials are aligned with the motion of the tissue to maximize the vectorial impact of the force thereon.

While the construct may be deployed within the body via open surgical procedures, preferably a minimally invasive method is used to deliver and deploy the material to the ectoluminal surface. Exemplary methods include, but are not limited to, minimally invasive incisions, laparoscopic procedures, trocar procedures, robotic interventions, or "NOTES" procedures or transvascular procedures, or percutaneous procedures.

ii. Endoluminal

The material may be attached to an endoluminal surface to power one or more devices implanted inside a patient's body. In these embodiments, the energy harvesting material is typically placed along the wall of the lumen and the piezoelectric materials are typically aligned such that in use they are normal to the pressure exerted by the flow through the lumen and parallel to the flow within the lumen. Alternatively variations may exist with the material placed normal to or at some angle within 0-90° of alignment with the flow. Additionally, in some embodiments, the material may be placed within the lumen, i.e. within the actual flow path. The various configurations described herein can be combined, such that a first energy harvesting material is placed in one direction relative to the flow within the lumen and a second (or third, or more) energy harvesting material is placed in a different direction relative to the flow within the lumen.

With these constructs, the pulsatility of the flow and/or shear force are converted into electrical energy by the MEH material(s) or system thereof. The system, device or material can therefore capture and convert mechanical energy from pressure or wave motion—longitudinal, transverse, standing, or surface, or shear or frictional forces. Further any combination of these may be utilized to enhance capture.

Also the degree of capture may therefore me tuned by arranging the capturing system to selectively capture or pick up part of these mechanical forces, i.e. one can tune the degree of energy capture through careful planning of the vectorial and spatial alignment (taking into account these various directional forces, waves shear, etc. so as to use this as a means of going from 100% (max) capture to 0% (min) capture.

1. Pulsatility

Pulsed flow through the lumen and along the energy harvesting material could be converted into electrical energy by the MEH material(s).

2. Continuous Flow

Continuous flow e.g., either laminar, turbulent, swirling or any means or combination, through the lumen and along the energy harvesting material could be converted into electrical energy by the MEH material(s). For example, a continuous flow device, such as a continuous flow left ventricular assist device (LVAD), right ventricular assist device (RVAD), or biventricular assist device (BIVAD) could be powered by the MEH material(s) or a system thereof implanted in a ventricle.

3. Smart Stents

Smart responsive implants, including smart stents, that are able to sense and respond to their environment, are described in U.S. Pat. No. 6,802,811 to Slepian, the disclosure of which is incorporated herein by reference. These smart materials require a power source and could be modified to use the energy harvesting materials described herein as a power source.

4. Methods of Delivery of MEH Materials and Systems Thereof Endoluminally

Constructs containing one or more mechanical energy harvesting materials may be deployed via open surgical methods or more typically via cather-based percutaneous techniques, such as used in interventional cardiology or radiology or minimally invasive surgery.

b. Non-Biologics

The systems and materials described herein may be used to power biological devices and machines or devices, and systems to aid, monitor, interrogate, sense, modify, treat or otherwise interact with nonbiologic or biological or biohybrid systems. The systems may be configured to contact and conform to the surface of any device, and are well-suited to conform to non-uniform surface with curves or undulations. As described above with respect to application to biological surfaces, when the system is applied to the surface of a non-biological device or machine, it is able to efficiently convert the mechanical stress produced by the device or machine to electrical energy, which may be used to power the same device or machine or a different one. Optionally, the system may be configured to store the electrical energy that it produces.

V. Methods of Making Materials

Methods for forming piezoelectric materials on flexible substrates are known. Suitable methods are described for example in X. Feng, et al., "Stretchable Ferroelectric Nanoribbons with Wavy Configurations on Elastomeric Substrates", *ACS Nano*, 5 (4): 3326-3332 (2011) and Y. Qi, et al., "Piezoelectric Ribbons Printed onto Rubber for Flexible Energy Conversion," *Nano Lett.*, 10: 524-528 (2010).

The preferred method for manufacturing a mechanical energy harvesting material containing PZT ribbons produces materials with the highest levels of strain during bending, but does not exceed the maximum facture level of PZT during bending. These materials are able to produce the greatest amount of power during bending processes, such as when placed on a biological surface that moves regularly (e.g., the heart, lungs, or outer surfaces such as the hands, arms, legs, or feet, etc of a human or non-human mammal).

A preferred method for making PZT ribbons embedded in capacitor type structures is described in Example 1 and more generally described below. The steps in this method are also illustrated in FIGS. 1A-D.

A multilayer stack of PZT, a suitable material for the bottom electrode (e.g. PT/Ti), and silicon dioxide ($SiO_2$) is coated on a silicon wafer. See FIG. 1A.

PZT ribbons with suitable thicknesses (such as from about 100 nm to about 10 microns) and dimensions are etched via chemical etching to a hard-baked mask of photoresist.

The top electrode is formed by depositing a suitable inert, conductive material, such as gold, platinum, or both on the PZT surface of the multilayer stack. The top and bottom electrodes of the PZT ribbon are defined by photolithography, such as via chemical etching through a hard-baked mask of photoresist.

The resultant ribbons are protected by a hard-baked photoresist during partial removal the removal of a sacrificial layer underneath the PZT ribbon. See FIG. 1B. In this method the silicon dioxide layer is the sacrificial layer.

The PDMS stamp is contacted with the ribbon. See FIG. 1C.

Figure 1F:
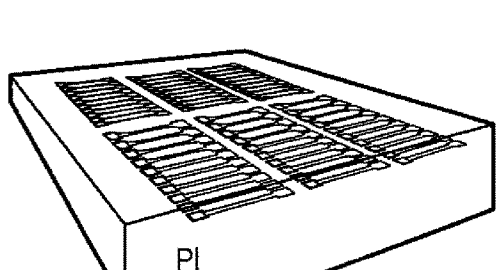

Then the multilayered PZT containing devices are removed from the silicon wafer, such as by peeling them off of the silicon wafer, and placed on a suitable substrate having the desired Young's modulus, typically a high Young's modulus. In FIG. 1F, the multilayered PZT containing devices are transferred to a PI substrate.

Finally, the entire device is coated with an inert, biocompatible material, such as a layer of PI, which isolates the MEH materials from bodily fluids and tissue, thereby minimizing the risks of failure or rejection.

Contact holes for the top and bottom electrodes are formed, and connection lines for the electrodes are prepared using known methods.

EXAMPLES

Example 1. Fabrication of PZT Ribbons Array and Transferprinting them on PI

PZT ribbons embedded in capacitor type structures with top and bottom electrodes were fabricated as follows. The top electrode was formed by deposition of Au/Cr (200 nm/10 nm) with an electron beam evaporator on the surface of a multilayer stack of $Pb(Zr_{0.52}Ti_{0.48})O_3/Pt/Ti/SiO_2$ (500 nm/300 nm/20 nm/600 nm; INOSTEK) on a silicon wafer. Coating the wafer with photoresist (PR, AZ5214E) followed by patterning by photolithography defined the top electrode areas (50 μm×2 mm) for each PZT ribbon.

Au and Cr layers were etched with gold etchant (TFA, Transene Company Inc., USA) and CR-7 chrome etchant (OM Group, USA), respectively.

PZT ribbons with thickness of 500 nm and an area of 100 μm×2.02 mm were created by wet chemical etching with $HNO_3$ (nitric acid): BHF (buffered hydrogen fluoride): $H_2O$ (DI water)=4.51:4.55:90.95 through a hard-baked mask of photoresist (PR) (AZ4620, Clariant) (See FIG. 1A). The hard baking involved 80° C. for 5 minutes, 110° C. for 30 minutes and then 80° C. for 5 minutes (See FIG. 1B).

The bottom Pt/Ti electrode with area of 140 μm×2.02 mm was patterned by wet chemical etching with HCl (hydrochloric acid): $HNO_3$: DI water 3:1:4 at 95° C. through a hard baked mask of AZ4620. The PZT layers were protected by photolithographically patterned with photoresist (PR) during partial removal of the sacrificial layer, $SiO_2$ with dilute HF (hydrofluoric acid) (DI water: 49% HF=1:3). The hard baked photoresist mask was completely removed in an acetone bath for 3 hours after etching the $SiO_2$.

A PDMS stamp for transfer was fabricated by casting a mixture of PDMS (Sylgard 184, Dow Corning; 10:1 ratio of prepolymer to curing agent) in a plastic petri dish, and curing at room temperature for 24 hours. Next, the stamp was conformally contacted on the top of the ribbons (See FIG. 1C). The devices were retrieved by peeling the stamp away from the Si wafer and then transfer printed on a film of PI (75 μm, DuPont, USA). This film was formed by spin-coating a layer of poly(pyromellitic dianhydride-co-4, 4'-oxydianiline) auric acid solution, to a thickness of 1.2 μm (See FIG. 1F).

The printed PZT ribbons on the PI were spin-coated with another layer of PI for encapsulation and hard baked at 250° C. in a vacuum oven.

To open contact holes for the top and bottom electrodes, the device on PI was patterned with photoresist (PR, AZ 4620), and developed with diluted AZ®400K developer (AZ Electronic Materials, USA) (deionized water (DI):400 K developer=1:2). The PI was etched in reactive ion etching (RIE, March) to open contact holes. Connection lines were obtained by the deposition of Au/Cr (200 nm/10 nm) using electron beam evaporation.

The interconnection lines were spin-coated with another layer of PI for encapsulation and hard baked at 250° C. in a vacuum oven.

Example 2. Poling of the PZT Thin Film and Device Analysis Via Mechanical Testing The PZT thin films sandwiched between Ti/Pt (20 nm/300 nm) bottom electrode and Cr/Au (10 nm/200 nm) were poled with an electric field of 100 kV/cm at 150° C. for 2 hours. A semiconductor parameter analyzer (4155C, Agilent) was used to measure the open voltage and short current values of mechanical energy harvester.

A mechanical bending stage was used for testing the PZT MEH. The system includes a high precision linear stage (ATS100-150; Aerotech, Inc.; USA), equipped with precision ground ball screw, noncontact rotary encoder with 1000 line/rev, and brushless servomotor to achieve a motion with an accuracy of ±0.5 μm and a bidirectional repeatability of ±0.3 μm over 150 mm stage motion range. The stage can achieve velocities up to 100 mm/sec with maximum side load of 100 N in horizontal configuration. The stage motion was controlled with a Soloist single axis PWM digital controller (SOLOISTCP20; Aerotech, Inc.; USA) and USB interface. Additionally, two U-Form Vise grip (TH240k, Grip Engineering Thümler GmbH; Germany) were attached to the stage. Pyramid shape jaws (TH240k-BP, Grip Engineering Thümler GmbH; Germany) were attached to the vices to achieve maximum tensile gripping force of 2.5 kN of the specimen during the test. A LabVIEW (National Instruments Corporation; USA) based program was designed to control the stage to perform the test cycle.

The flexibility of the MEH materials was also tested on different curved surfaces, such as balloons, a finger and a wrist.

Results

Measurements with a bending stage revealed the dynamic mechanical properties for these materials. FIG. 3A illustrates 3D deformations of the PZT ribbons, with distributions of strain obtained by finite element analysis (FEA). The overall shapes match those observed on the bending stage. The strain distributions (Figures not shown) for the different deformations illustrate the nature of deformations in the various device layers. The results determine the electrical field and electrical displacement in the PZT through constitutive models of piezoelectric behavior. The voltage and current outputs of a representative device before (FIGS. 3C and 3D) and after (FIGS. 4B and 4C) rectification illustrate the nature of operation.

The computed bending stiffness (per unit width) was 0.22 Nmm and 0.10 Nmm for regions coincident with and away from the PZT structures, respectively. For a bending radius of 2.5 cm, the maximum strain in the PZT was only 0.1%.

Additional in vitro characterization illustrates that these MEH devices can be wrapped onto various curved objects such as balloons, fingers and wrists.

Control experiments revealed that reversing the electrical connections to measurement equipment reverses the signal polarity. The devices exhibit excellent fatigue properties. Bending and releasing more than twenty million times while in direct contact with a transparent layer of gelatine (Knox), to mimic a moist environment, induced no noticeable degradation in the properties.

Analytical Model

The observations described above were captured with an analytical model. Compression of a device with length L leads to buckling (i.e. bending) with an out-of-plane displacement w=A[1+cos (2πx$_1$/L)]/2 as shown in FIG. 2A, where the origin of coordinate x$_1$ is at the center of the device, and the amplitude A is related to the compression ΔL between the two ends by A≈(2/π)$\sqrt{L \cdot \Delta L}$. The PZT layers, together with the top and bottom electrodes, bend with the buckled substrate. The membrane strain in the PZT ribbons is given analytically $$\varepsilon_m = 4\pi \frac{\overline{EI}_{PI}}{\overline{EI}_{comp}} \frac{h}{L} \sqrt{\frac{\Delta L}{L}}, \quad [1]$$

where $\overline{EI}_{comp}$ and $\overline{EI}_{PI}$ are the bending stiffness (per unit width) of the PI with and without the PZT and electrodes, respectively; and h is the distance from the center of the PZT layers to the neutral mechanical plane of the cross section as shown in FIG. 2B. The bending strain in the PZT ribbons has opposite signs above and below the midpoint through the thickness of the PZT, and therefore does not contribute to the voltage or current output. For thin PZT layers, the bending strain is much smaller than the membrane strain; the total strain is therefore dominated by the membrane strain.

PZT is transversely isotropic with the polarization direction x$_3$ normal to the surface. The elastic, piezoelectric, and dielectric constants are denoted by c$_{ij}$, e$_{ij}$, and k$_{ij}$, respectively. For plane-strain deformation (ε$_{22}$=0) the strain ε$_{33}$ and the electrical field E$_3$ along the polarization direction x$_3$ satisfy the constitutive relations 0=c$_{11}$ε$_{11}$+c$_{13}$ε$_{33}$−e$_{31}$E$_3$ and D$_3$=e$_{31}$ε$_{11}$+e$_{33}$ε$_{33}$+k$_{33}$E$_3$, where the electrical displacement D$_3$ along the polarization direction is a constant to be determined. For measurements of current, the top and bottom electrodes connect to an ammeter, which has negligible electrical resistance. As a result, voltage between the top and bottom electrodes is zero, and D$_3$=$\bar{e}$ε$_m$, where the effective piezoelectric constant is $\bar{e}$=e$_{31}$−(c$_{13}$/c$_{33}$)e$_{33}$ and the membrane strain ε$_m$ is given in Eq. 1. For each group of devices in series, the charge induced by ε$_m$ gives the current I=−A$_{PZT}$$\dot{D}_3$, i.e., $$I = (-\bar{e}) A_{PZT} \frac{d\varepsilon_m}{dt}, \quad [2]$$

where A$_{PZT}$ is total area of the PZT ribbons in each group. In the Examples, the compression ΔL between the two ends of the device is a periodic function of time t, given by $$\Delta L = \begin{cases} \frac{\Delta L_{max}}{4}\left[1-\cos\left(\frac{\pi t}{T_1}\right)\right]^2, & 0 \le t < T_1 \\ \Delta L_{max}, & T_1 \le t < T_1+T_2 \\ \frac{\Delta L_{max}}{4}\left\{1-\cos\left[\frac{\pi(t-2T_1-T_2)}{T_1}\right]\right\}^2, & T_1+T_2 \le t < 2T_1+T_2 \\ 0, & 2T_1+T_2 \le t < 2(T_1+T_2) \end{cases} \quad [3]$$

in the first period, where ΔL$_{max}$ is the maximum compression, and T=2(T$_1$+T$_2$) is the period.

FIG. 3B shows ΔL vs. t for T$_1$=0.8 second, T$_2$=1.3 second, and ΔL$_{max}$=1.5, 3, 5 and 10 mm as was observed in the experiments. FIG. 3D shows that the current obtained from Eq. 2 for these four values of ΔL$_{max}$ agreed well with the data in the experiments, where L=2.5 cm, $\overline{EI}_{PI}$/$\overline{EI}_{comp}$=0.45, h=24.7 μm and A$_{PZT}$=2.24 mm$^2$ as in experiments, and $\bar{e}$=10 C/m$^2$, which is on the same order of magnitude as the literature values (Park & Sun, "Effect of electric-field on fracture of piezoelectric ceramics," *Int. J. Fract.*, 70:203-216 (1995)). The peak current ranged from 0.06 μA to 0.15 μA for ΔL$_{max}$ from 1.5 to 10 mm, respectively In measurements of voltage, the potential drop across each group is V/N, where V is the total voltage for N groups of devices in series. The electrical displacement is D$_3$=$\bar{e}$ε$_m$+$\bar{k}$V/(Nt$_{PZT}$), where $\bar{k}$=k$_{33}$+(e$_{33}$$^2$/c$_{33}$) is the effective dielectric constant and t$_{PZT}$ is the thickness of PZT ribbons. The current I=A$_{PZT}$$\dot{D}_3$ is related to the voltage V and resistance R of the voltmeter by I=V/R, which gives V/R=A$_{PZT}$$\dot{D}_3$, i.e., $$\frac{dV}{dt} + \frac{Nt_{PZT}}{A_{PZT}R\bar{k}}V = \frac{N\bar{e}t_{PZT}}{\bar{k}} \frac{d\varepsilon_m}{dt}. \quad [4]$$

For the initial condition V (t=0)=0, the voltage is given by $$V = \frac{(-\bar{e})Nt_{PZT}}{\bar{k}} e^{\frac{Nt_{PZT}}{A_{PZT}R\bar{k}}t} \left| \int_0^t \frac{d\varepsilon_m}{dt} e^{\frac{Nt_{PZT}}{A_{PZT}R\bar{k}}t} dt \right|. \quad [5]$$

For R=60×10$^6$Ω in the experiment and $\bar{k}$=4×10$^{-8}$ C/Vm (Park & Sun (1995)), FIG. 3C shows the voltage V versus time t obtained from Eq. 5, which agrees well with experiments, including both the shape and peak value. The peak voltage can reach values as large as 3.7 V for the maximum compression ΔL$_{max}$=10 mm.

Without being bound by theory, it is believed that the differences between the measured and predicted behavior of the output current in FIG. 3D arise because, according to Eqs. 1 and 2, the current is directly proportional to the rate of compression dΔL/dt, and is therefore sensitive to dΔL/dt when the compression reverses direction. However, the assumed displacement profile does not follow precisely the one in the experiment. By contrast, the voltage is relatively insensitive to dΔL/dt because Eqs. 1 and 5 involve the integration of dΔ/dt.

Example 3. In Vitro Biocompatibility Assessment of the Flexible PZT MEH

Aortic smooth muscle cells (SMC) were harvested from albino Sprague-Dawley rat (with IACUC approval protocol from the University of Arizona) and subsequently cultured in Dulbecco's Modified Eagle Medium (DMEM) supplemented with 10% (v/v) fetal calf serum, 2% (v/v) of 0.2 M glutamine, 1% (v/v) of antibiotic/antimycotic solution. All cell culture supplements and medium were either purchased at Invitrogen (Grand Island, N.Y., USA) or BioWhittaker (East Rutherford, N.J., USA). SMCs were then sub-cultivated and cultured in an incubator at 37° C., 5% $CO_2$, and 95% relative humidity to passages 2-5 before subjecting to ribboning (trypsin-EDTA), cell counting, and seeding on the sterilized fibronectin (BD-Biosciences, San Jose, Calif., USA) coated PZT MEH.

To prepare for biocompatibility studies, PZT MEH ribbons were cut into 1 cm$^2$ coupons to fit in a 24-well culture plate. These coupons were then cleaned using Basic Harrick Plasma (Ithaca, N.Y., USA) for 10 minutes at 1 torr to increase surface hydrophobicity. Subsequently, coupons were sterilized under UV light for 30 mins then coated with 150 µl of 1 mg/ml fibronectin for another 15 mins. Any excess fibronectin was removed and allowed to dry in the culture hood for another 15 mins prior to $5 \times 10^4$ SMCs cultivation for 1, 3, and 9 days at 37° C., 5% $CO_2$, and 95% relative humidity. Medium was changed every 24 hours.

At the given latter endpoints, SMCs were stained using actin cytoskeleton/focal adhesion staining kit (Millipore, Mass., USA). Cells were fixed with 4% paraformaldehyde for 15 min, then washed and permeated the membrane with 0.05% Triton X for 5 min. Cells were washed and blocked with 1% protein standard (fractionated bovine serum albumin) in PBS at pH7.4 and subsequently stained with anti-vinculin for 1 hour at room temperature. Cells were washed and stained with fluorescein isothiocyanate conjugated mouse anti-immunoglobulin G (mIgG-FITC) to label vinculin and tetramethyl rhodamine isothicyanate (TRITC) conjugated Phalloidin to selectively label F-actin. After washing off all the excess stains, cells were then mounted in vector shield with DAPI and imaged using the Nikon ClSi Laser Scanning Confocal Fluorescence Microscope. SMCs on the PZT MEH exhibit normal morphology where intact cytoskeletal fibers, nucleus, and focal adhesion points are present, suggesting that the surface of PZT MEH is a suitable environment for cell growth.

Scanning electron microscopy (SEM, FEI Inspec S, Thermo, Rockford, Ill., USA) was also utilized to physically demonstrate the adherent of cells on PZT MEH ribbons.

Briefly, SMCs after 9 days of culture were fixed in 5% Glutaraldehyde in PBS at pH7.4 (100% fixator) then subjected to a graded series of water and ethanol (100% fixator→3:1→1:1→1:3→100% Distilled water→3:1→1:1→1:3→100% Ethanol). Samples were soaked for 5 min at each step. Finally, Samples were freeze-fried using critical point drying (CPD, EMS #3100, Hatfield, Pa., USA). A more detailed CPD protocol is described in Thomasson & Thomasson, "A comparison of CPD (critical point drying) and HMDS (hexamethyldisilazane) in the preparation of *Corallorhiza* spp. rhizomes and associated mycorrhizae for SEM (scanning electron microscopy)", *Transactions of the Kansas Academy of Science*, 114:129-134 (2011). Subsequently, samples were sputter-coated with gold at about 5-8 nm thick and imaged at 30 kV with aperture spot size of 3.

To evaluate the biocompatibility of the PZT MEH structures, the viability and cytotoxicity of SMC were determined after 9 days of cultivation by utilizing two color fluorescence LIVE/DEAD viability (Invitrogen) assay and Lactate Dehydrogenase (LDH) assay (Thermo, IL, USA), respectively. For LIVE/DEAD assay, SMCs grown on PZT MEH ribbon after 9 days were prepared and stained according to manufacture protocol with the exception that samples were mounted in Flouroshield containing DAPI (Sigma Aldrich, St. Louis, Mo., USA). Briefly, the culture medium was aspirated from each of the wells then rinsed three times with 1×PBS, and a working solution (consisting of 5 mL 1×PBS, 10 µL of 2 mM EthD-1, and 2.5 µL of 4 mM Calcein AM) was added to cover each of the samples. The submerged samples were incubated for 30 minutes at 37° C. After the incubation period, the working solution was removed, and the samples were rinsed once with 1×PBS, then mounted and immediately imaged with the Nikon ClSi fluorescence microscope.

For the LDH cytotoxicity assay, 50 µL medium from cells grown on fiber surfaces at the latter given endpoints (i.e., 1, 3, and 9 days) were mixed with 50 µL reaction mixture (prepared according to the manufacturer's recipe) in a 96-well plate for 30 minutes at room temperature. Stop solution (50 µL) was added and the plate was read at 490/680 nm. Mean percent of healthy cells was reported with standard error of mean.

All statistical analysis was performed using Microsoft Excel 2010. TTEST was analyzed using one-tailed distribution and two-sample unequal variance type. Statistical significance of differences between the means was determined using a student's t-test (p=0.05).

Results

SMCs readily adhere to fibronectin-coated structures, with evident spreading, and intact detectable cytoskeletal structures, i.e. focal contacts via fluorescence (green (viculin)) and cytoskeletal actin microfilaments (red). Scanning electron microscope (SEM) image showed spreading cells. No detectable cytotoxicity was observed in a live/Dead™ assay that identifies calcein AM (green) for viable cells and ethidium homodimer (red) for damaged cells, suggesting that the majority of SMCs are healthy (green). In fact, more than 96% of cells were viable after 9 days of culture. Cells grown on device structures show no differences from those grown on standard tissue culture plates at days 3 and 9 as seen by comparing the % of healthy cells at days 3 and 9 in the control (tissue culture dish) with those in the PZT energy harvester.

Encapsulation of these devices with biocompatible materials isolated them from bodily fluids and tissue, thereby minimizing the risks of failure or rejection. The thin spin-cast layer of polyimide (PI) served effectively in this role, as demonstrated in leakage tests performed in phosphate buffered saline (P-5368, pH 7.4, SIGMA), in a way that maintains excellent mechanical flexibility.

Example 4. Implantation of the PZT MEH: An In Vivo Study

All animals received humane care and were handled in accordance with IACUC approval protocol at the University of Arizona Animal Care Center. Male Corriente bovine (n=4, 90-140 Kg) and domestic ovine (n=1, 45 Kg) were used. Animals fasted for 12 hours without food and 8 hours without water prior to left thoracotomy. Animals were operated off-pump, without cardiopulmonary bypass and survived for two hours post-surgery.

Briefly, animals were restrained with Telazol (2.2 mg/kg Intramuscular (IM) or 4 mg/kg Intravenous (IV)), weighed, and anesthetized with 3-5% Isoflurane induction administered via the facemask. An oral endotracheal tube was then placed. Butorphanol (0.01-0.02 mg/kg) and Xylazine (0.1-0.2 mg/kg) were administered via intramuscular (IM) injection into the hamstring muscle to relieve pain. Animals were clipped, shaved, and prepped for the surgery. Glycopyrrolate was administered at 0.002-0.005 mg/kg Intravenous (IV) when bradycardia was present. The Animal was then intubated and anesthesia was further maintained at 0.5-3% Isoflurane and at room temperature throughout the study. An orogastric tube was placed to decompress the rumen. A triple lumen catheter (7-8F) was inserted percutaneously into the right jugular vein for IV line for drip infusion of lactated ringers to maintain hydration and for delivery of drugs. An arterial pressure catheter was placed in the carotid artery and ECG was connected to monitor the animal.

Prior to surgery, Ketamine (3-4 mg/kg) and Midazolem (0.25 mg/kg) were inducted intravenously to relax muscle. Pancuronium Bromide (0.04-0.1 mg/kg, IV) were used to block myoneural junctions. Fentanyl (loading dose of 5 µg/kg and dripping dose of 5 to 10 µg/kg/hr), Lidocaine (loading dose of 2 mg/kg and dripping dose of 2 mg/kg/hr), and Ketamine (loading dose of 2 mg/kg and dripping dose of 2 mg/kg/hr) were infused intravenously in addition to inhalant throughout the operation. Left thoracotomy was performed and cauterized with the electrosurgico knife (Conmed Excalibur Plus, Utica, N.Y., USA). The fifth left rib was snipped and a retractor was used to expose solid tissues like the heart, lung, and diaphragm. Amiodarone (loading dose of 50 mg IV bolus and dripping dose of 0.3 to 0.9 mg/kg/hr) was administered to control arrhythmias prior to the manipulation of the heart.

PZT MEH was then sutured to solid tissues using 2-0 bladed polypropylene (Ethicon, San Angelo, Tex., USA). A cable (ACF; Anisotropic conductive film, 3M Co.) was connected to a voltmeter storage monitor systems. To evaluate the responsiveness of the PZT MEH, temporary pacemaker (Medtronic 5388, Minneapolis, Minn., USA) and Dobutamine (5-15 µg/kg/min, IV) was used to fluctuate the heart rate. After all initial readings, animals were survived for 2 hours to allow the PZT MEH to recharge the battery. Incision sites were closed using the standard technique. At the termination of the surgery, animal were humanely euthanized with 30 ml of Beuthanasia while still under general anesthesia. The PZT MEH was then removed for detailed examination and reading.

Results

In vivo testing involved affixing the devices to epicardial sites on the RV, LV base and free wall of bovine and ovine hearts. The anchoring scheme used sutures at three points, to maintain focal contact, though without rigid attachment so as to minimize any alteration or constraint on cardiac motion. Similar suturing techniques have been previously utilized to suture 3D patches onto the left ventricle in a rat model (Thai H M, et al., Implantation of a three-dimensional fibroblast Matrix Improves Left ventricular function and blood flow after acute myocardial infarction," *Cell Transplant,* 18(3):283-295 (2009)). Furthermore, alternative suturing techniques, including running locked stitch and 5-point lacerations can further reinforce the attachments.

No detectable change in cardiac conduction or epicardial motion occurred following this simple procedure for fixing the device onto the epicardium. The PZT MEH maintained conformal contact, without delamination from the heart, during the entire cycle of cardiac motion, from contraction to relaxation.

Figure 5A:
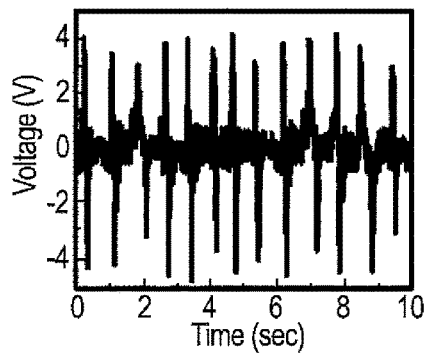
FIGS. 5A-5K.
Figure 5B:
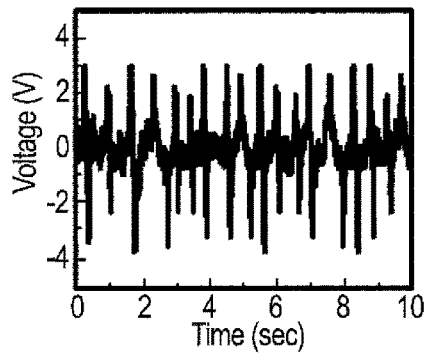
Figure 5C:
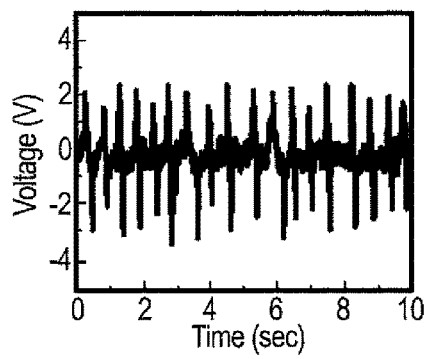
Figure 5D:
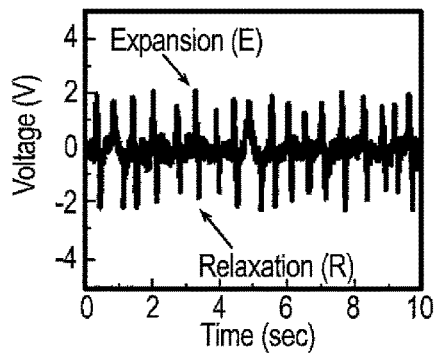
Figure 5E:
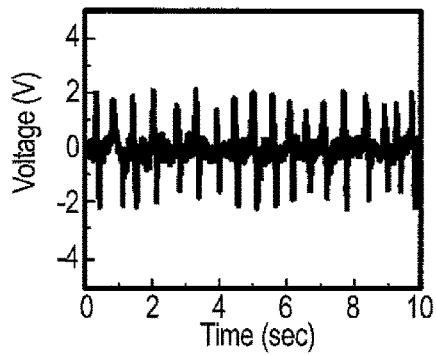

Evaluation of various mounting sites helped identify locations for maximum power extraction. Analysis of voltage outputs from devices placed on the RV, LV base and free wall are depicted in FIGS. 5A, B, and C, respectively. The RV yielded the best results, even though the LV has more muscular fibers (9-11 mm thick) than the RV (3-5 mm thick) (Hurst J W, et al., *Atlas of the heart,* Gower Medical (1998)). The differences in shape and other functional characteristics were, however, most important. The RV chamber is box- or wedge-shaped in form, with a concave free wall, which thinner than the LV and is attached to the convex interventricular septum (Fritz J, et al., "Right ventricle shape and contraction patterns and relation to magnetic resonance imaging finding," *J. Comp. Assist Tomogr,* 29 (6):725-733 (2005)). The LV is roughly cylindrical in shape and has a thick wall structure with three spiraling layers of muscle, to enable contractions with a twisting or torsional motion (Anzola J, "Right ventricular contraction", *Am. J. Physiol.,* 184:567-571 (1956); Baciewicz F A, et al., "Torsional ventricular motion and rotary blood flow", *Cardiac Chronicle* 5:1-8 (1991)). The RV ejects blood primarily by shortening of its free wall, while ejection from the LV primarily involves a reduction in its diameter or circumference, associated with wall thickening (Rushmer R F, "Length-circumference relations of the left ventricle", *Circ. Research,* 3:639-644 (1955)). The contraction of the RV by shortening the free wall likely results in enhanced overall wall motion and hence increased bending of the MEH compared to the twisting contraction of the LV.

Figure 5F:
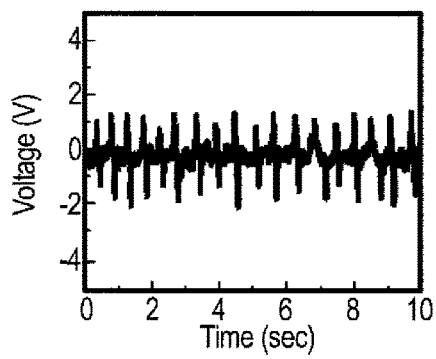
Figure 5G:
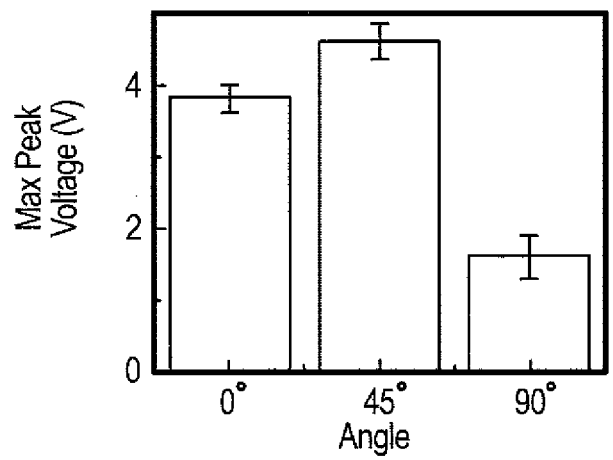

Orientation of the device was also seen to be important, as illustrated by the data in FIG. 5G. Bending in the longitudinal direction ($x_j$ direction) relative to the orientation of the PZT ribbons provided the highest efficiency.

To examine the dependence on orientation on the heart, measurements involve the longitudinal direction of PZT ribbons along 0°, 45° and 90° directions with respect to the apex of the heart. The 0° and 45° directions produced greater voltages than those for 90° (see FIG. 5O). This behavior, for 0° and 45°, was expected since the myocardial tissue of the heart is anisotropic and contracts in a generally circumferential direction (McHale & Greenfield, "Evaluation of several geometric models for estimation of left ventricular circumferential wall stress", *Circ. Research,* 33:303-312 (1973)) with cardiac fibers aligned in a continuous manner from +60° on the endocardium to −60° on the epicardium (Streeter & Hanna, "Engineering mechanics for successive states in canine left ventricular myocardium", *Circ. Research,* 33:639-655(1973)); 90° is clearly out of this range.

Theoretically, as shown in Eq. 5, the voltage is proportional to the strain rate, or equivalently, the strain amplitude for a given period. Finite element analysis (FEA) confirmed that the strain by bending along the $x_1$ direction is larger than that along $x_2$. Aligning the $x_1$ direction with the strongest bending direction produces the greatest amounts of the harvested energy.

Figure 5H:
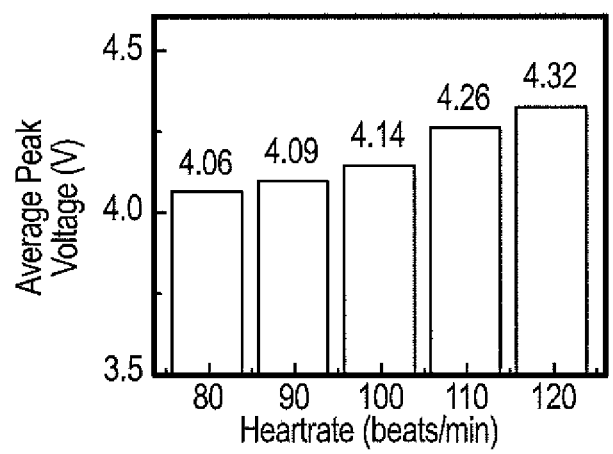
Figure 5I:
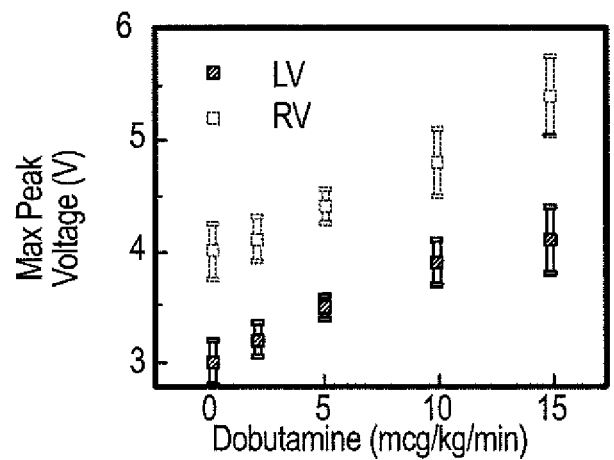
Figure 5J:
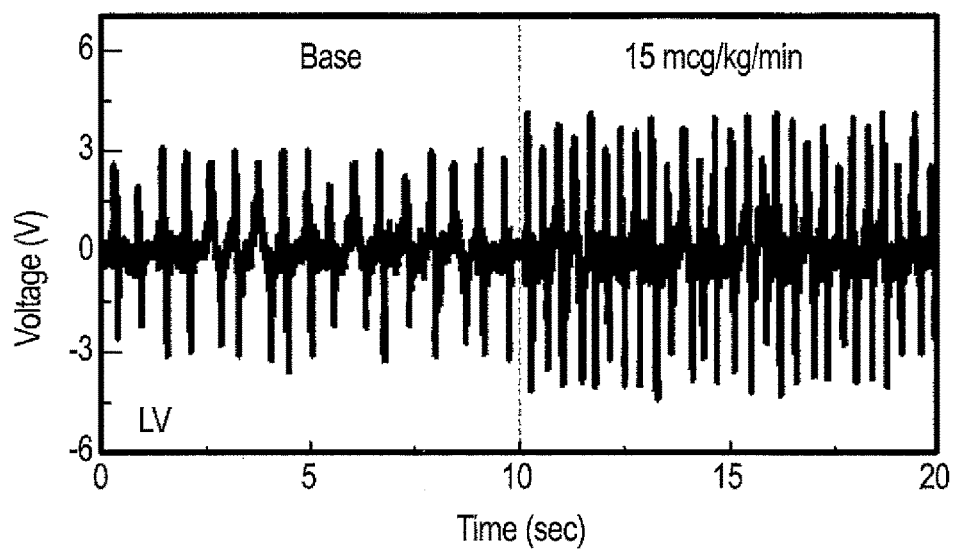
Figure 5K:
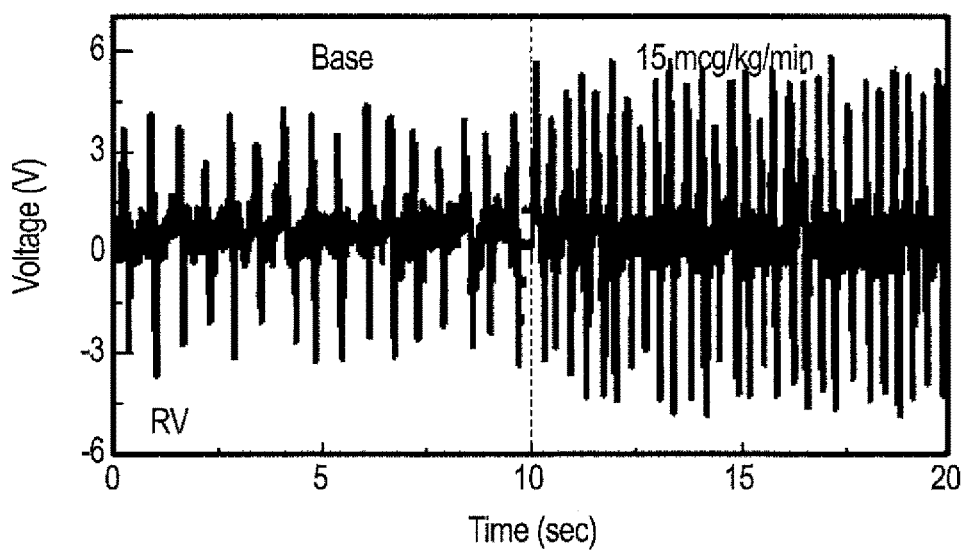
Figure 6A:
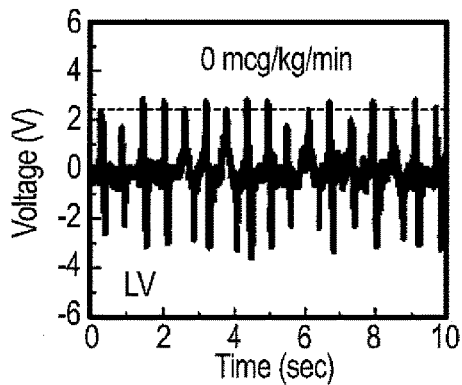
FIGS. 6A-6J are graphs illustrating the output from a PZT MEH mounted on the bovine heart for different levels of dobutamine infusion. The graphs show the voltage as a function of time measured from a PZT MEH on the LV (FIGS. 6A-6E), RV (FIG. 6F-6J) of a bovine heart at 0° with respect to the apex with 0, 2, 5, 10 and 15 mcg/kg/min of dobutamine. These graphs contain the data that is summarized in FIG. 5I.
Figure 6B:
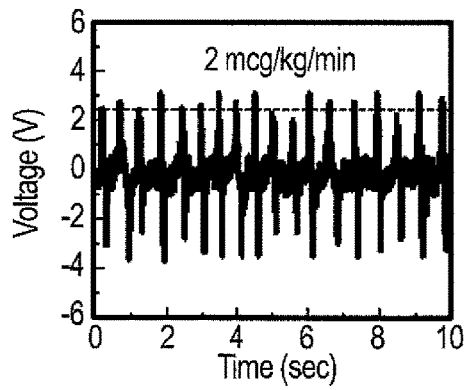
Figure 6C:
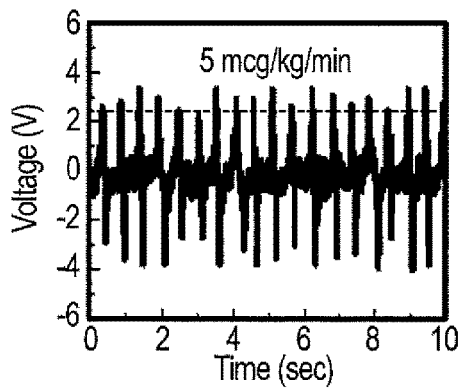
Figure 6D:
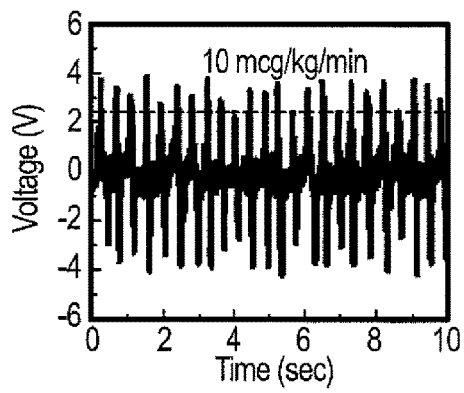
Figure 6E:
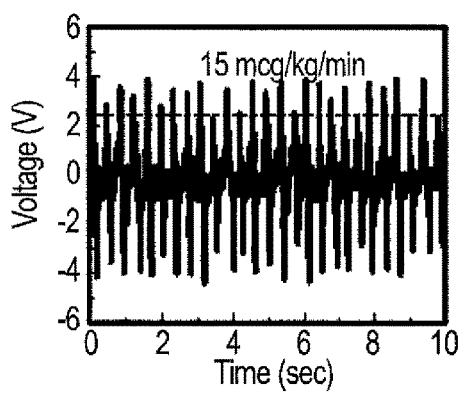
Figure 6F:
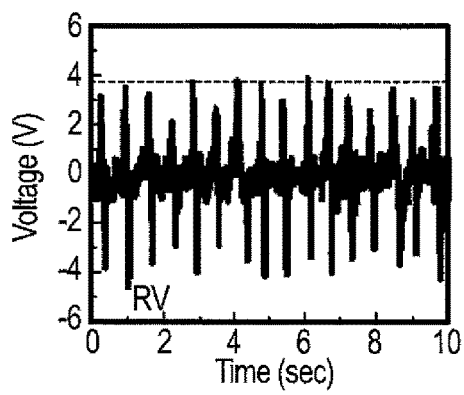
Figure 6G:
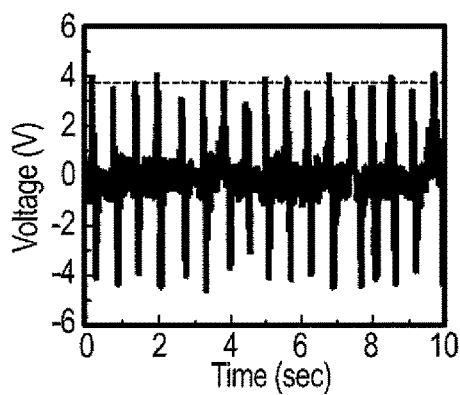
Figure 6H:
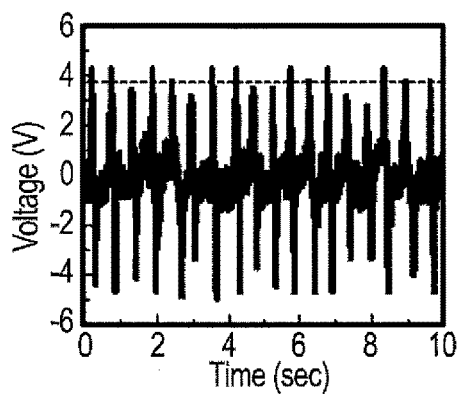
Figure 6I:
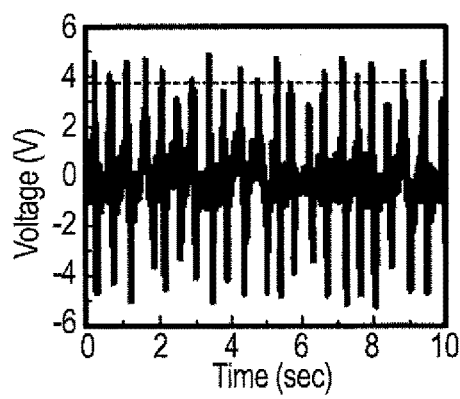
Figure 6J:
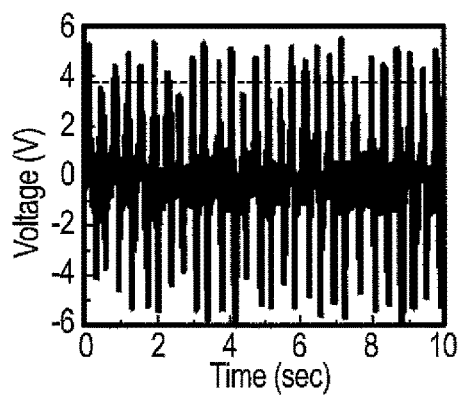

The size of the heart, the beat rate and the force of contraction are additional factors that affect voltage output. In the Examples, the bovine heart is nearly twice the mass of the ovine model. All devices deployed on the former yielded significantly higher voltage outputs than that those in the ovine model, for any site of implantation on the heart. Cf FIGS. 8A-B (bovine model) with FIGS. 9A-B (pig model). Modulating heart rate through electrical and chemical stimulation revealed the dependence on frequency. FIG. 5O demonstrates that increasing the bovine heart rate with a temporary pacemaker (Medtronic 5388, Minneapolis, Minn., USA) increased the voltage in direct proportion to heart rate. This result was consistent with modeling results, assuming that the amplitude does not vary significantly with frequency. Similarly, increasing the force and degree of contractility of the myocardium via Dobutamine infusion, i.e. the inotropic state (15 mcg/kg/min), increased both the voltage and the frequency of the output. Such a response occurs for both the LV and RV (see FIGS. 5F, 5G, and 5H).

Additionally, when the device was subjected to different heart rates, such as from 80 beats/min to 130 beats/minute, in both the ovine and bovine hearts, the device remained intact, was stable, and produced electrical energy regardless of its location on the heart.

Figure 7E:
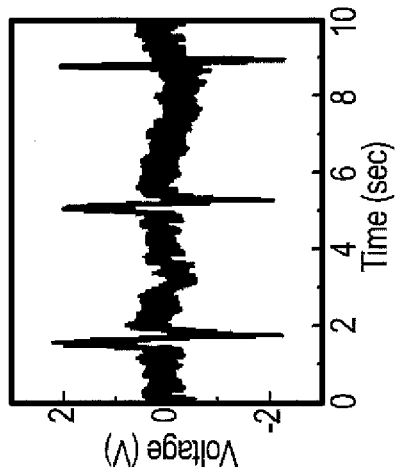
FIGS. 7A-7F are graphs showing in vivo evaluation of PZT MEHs on the lung and diaphragm.
Figure 7F:
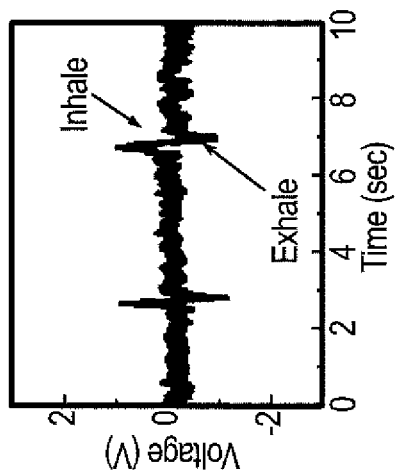
Figure 7B:
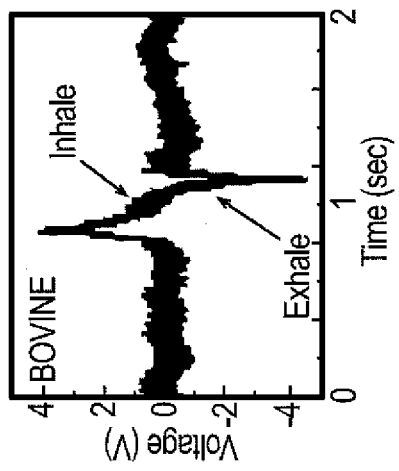
Figure 7D:
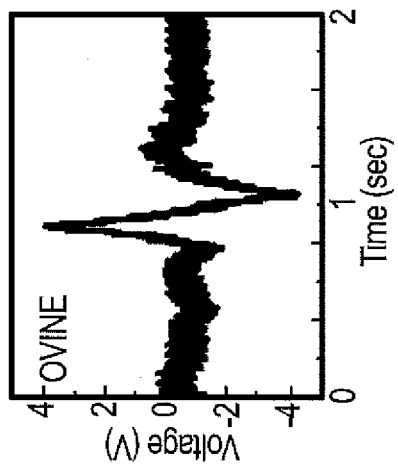
Figure 7A:
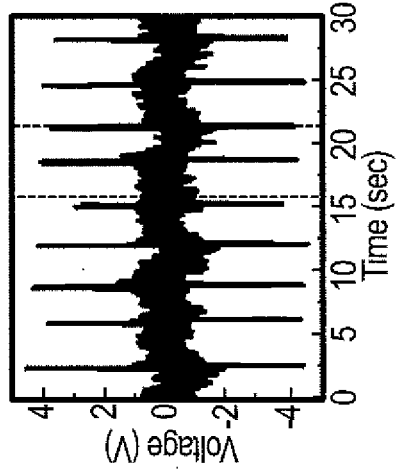
Figure 7C:
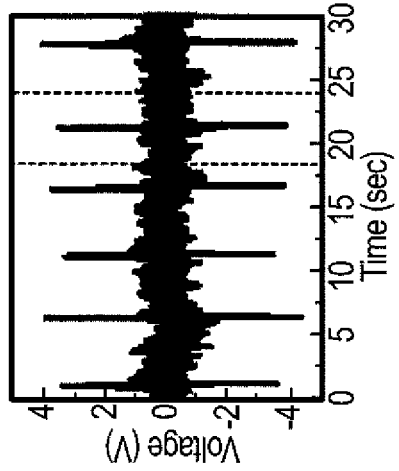

The lung represents another internal organ of interest for mechanical energy harvesting. Tests were conducted on both the bovine and ovine lung. In both models, it was observed that respiratory movement can be converted to voltage (FIGS. 7A and 7B). Unlike observations with the heart, data collected from the lung show no strong inter-species differences (FIGS. 7C and 7D).

The diaphragm offers an additional option for mechanical energy harvesting. Data indicate larger voltage response for the bovine than the ovine, as shown in FIGS. 7E and 7F, respectively.

Collectively, these results indicate that the MEH systems described herein are capable of harnessing energy from different locations across the body, with operational details that depend on the species and the organ.

Figure 8A:
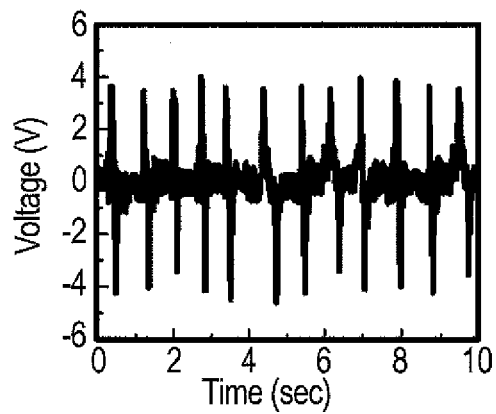
FIGS. 8A-8B are graphs showing the performance of a PZT MEH evaluated with the chest open and closed and scaling of power output in multilayer stacked designs. The graphs illustrate the voltage as a function of time for a PZT MEH on the bovine RV with the chest open (FIG. 8A) and closed (FIG. 8B).
Figure 8B:
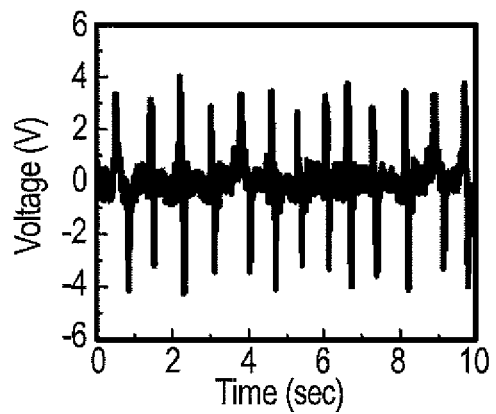
Figure 9A:
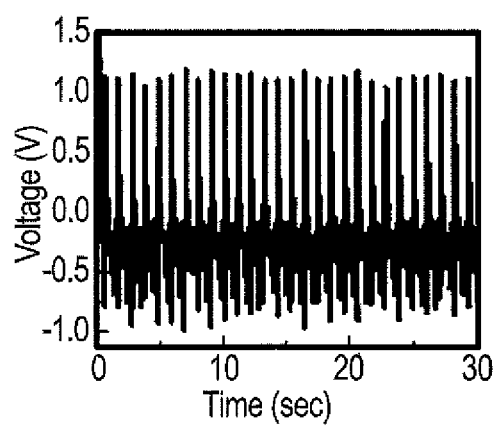
FIGS. 9A-9B are graphs illustrating the performance of a PZT MEH evaluated with the chest open and closed on a pig model. The graphs illustrate the voltage as a function of time for a PZT MEH on the pig LV with the chest open (FIG. 9A) and closed (FIG. 9B).
Figure 9B:
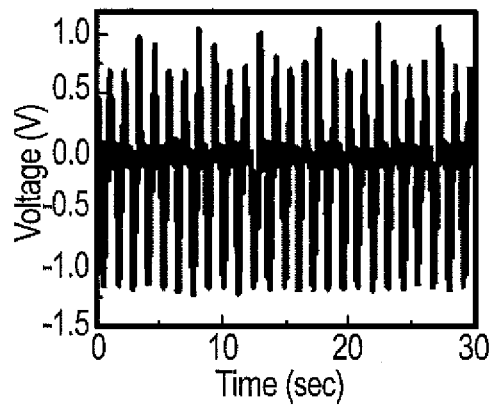

Any long-term practical use requires efficient operation upon closure of the chest post-thoracotomy. Data collected with the chest open and closed showed the same capabilities in power generation, such as seen in FIGS. 8A and 8B for the bovine model. Similar in vivo tests on a pig model appear in FIGS. 9A and 9B.

Example 5. FEA for the Deformation of the Stacks

Finite element analysis (FEA) is used to study the deformation of a single PZT MEH and the stacks of 3 and 5 PZT MEHs with spin-casted silicone layer of 10 μm thickness in between. The solid elements in the ABAQUS finite element program (5Dassault Systémes (2010) Abaqus analysis user's manual v.6.10. Dassault Systémes Simulia Corp., Rhode Island) were used to mesh all materials, including the PZT ribbons.

TABLE 1

The amplitude of the stacks for ΔL = 5 mm

|  | $n^{th}$ PZT MEH | Amplitude (mm) |
|---|---|---|
| single PZT MEH | 1 | 6.41 |
| stack of 3 PZT MEHs | 3 | 6.37 |
|  | 2 | 6.37 |
|  | 1 | 6.37 |
| stack of 5 PZT MEHs | 5 | 6.35 |
|  | 4 | 6.35 |
|  | 3 | 6.35 |
|  | 2 | 6.35 |
|  | 1 | 6.35 |

Table 1 shows that the amplitudes of the PZT MEHs in the stacks are very close to that of the single PZT MEH, with the difference less than 1%, which suggests that the soft silicone layers do not make significant contribution to the deformation of the PZT MEHs.

Figure 10A:
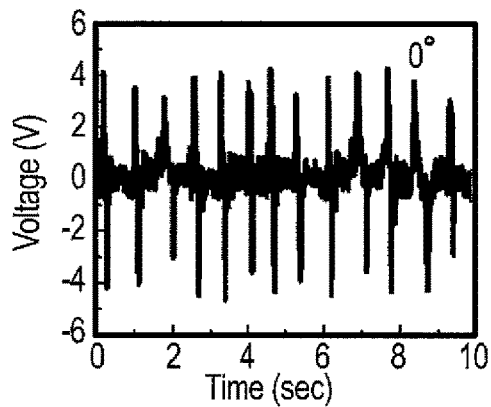
FIGS. 10A-10B are graphs showing the effect of orientation of the PZT MEH with respect to the apex of a bovine heart. Both graphs show the voltage as a function of time measured on the RV of a bovine heart with 80 beats/min at 0° (FIG. 10A) and at 45° (FIG. 10B).
Figure 10B:
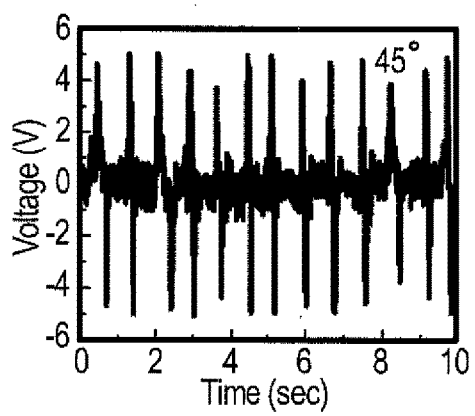

The power output of a PZT MEH depends on its design. With layouts described previously, the time-averaged power density (electrical power output per unit area of PZT) corresponds to 0.12 and 0.18 μW/cm² for mounting on the RV of a bovine heart at 0° and 45°, see FIGS. 10A and 10B, respectively.

Figure 11A:
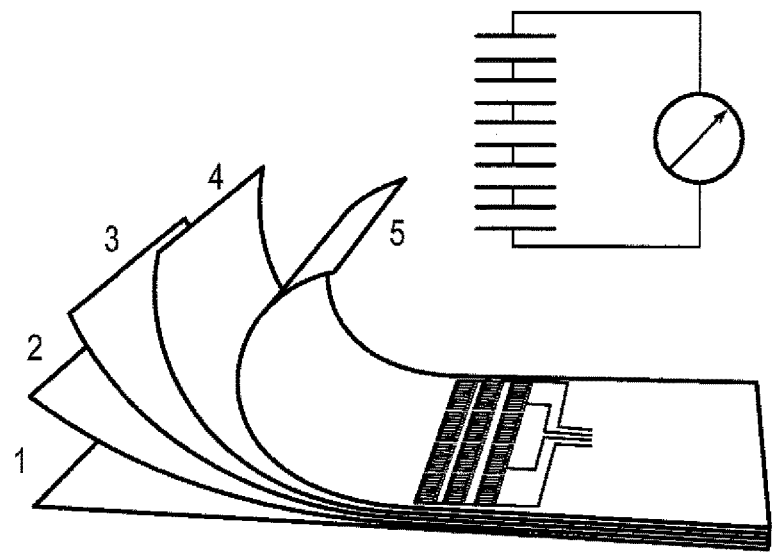
FIGS. 11A-11C show the performance of a PZT MEH evaluated for the scaling of power output in multilayer stacked designs.
Figure 11B:
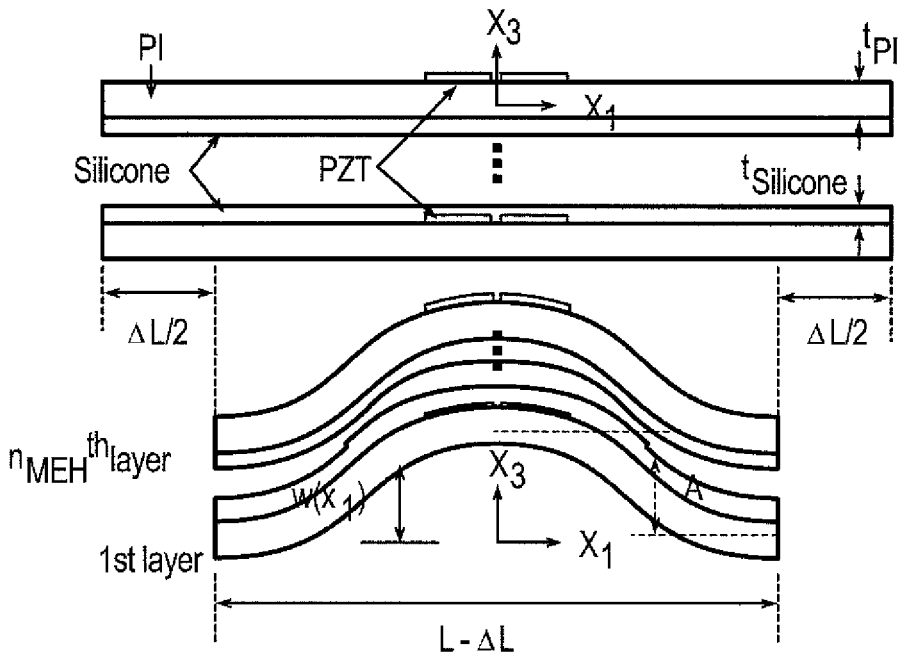
Figure 11C:
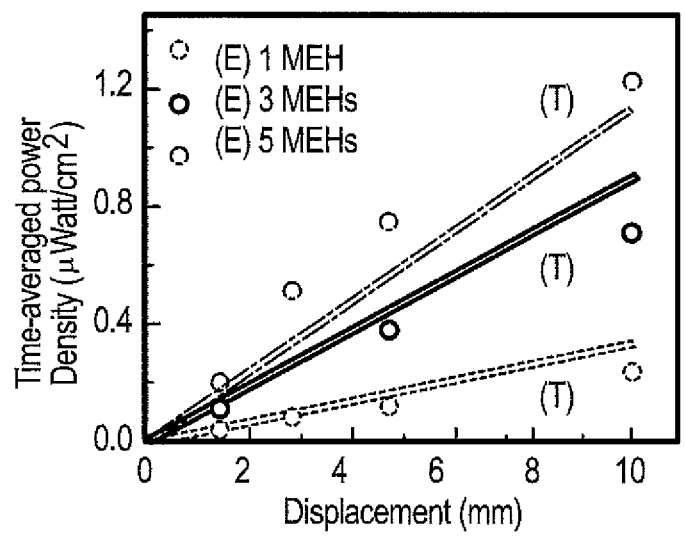
Figure 12A:
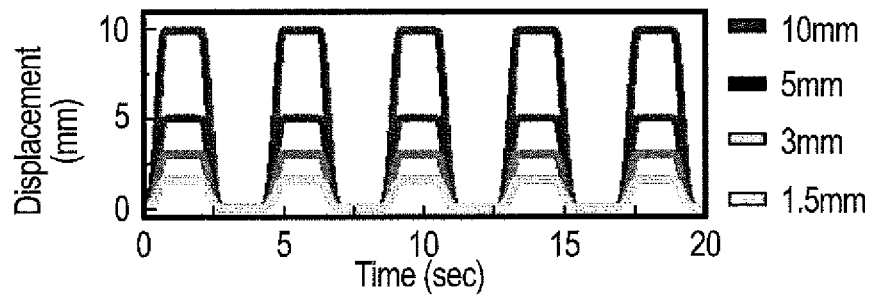
FIGS. 12A-12C contain graphs illustrating the output voltage as a function of time measured from a stacked arrangement of PZT MEHs. Experimental and theoretical results for displacement (FIG. 12A), voltage as a function of time (FIGS. 12B and 12C), for four different bending load displacements are shown. Spin-cast layers of silicone bond the separate PZT MEHs.
Figure 12B:
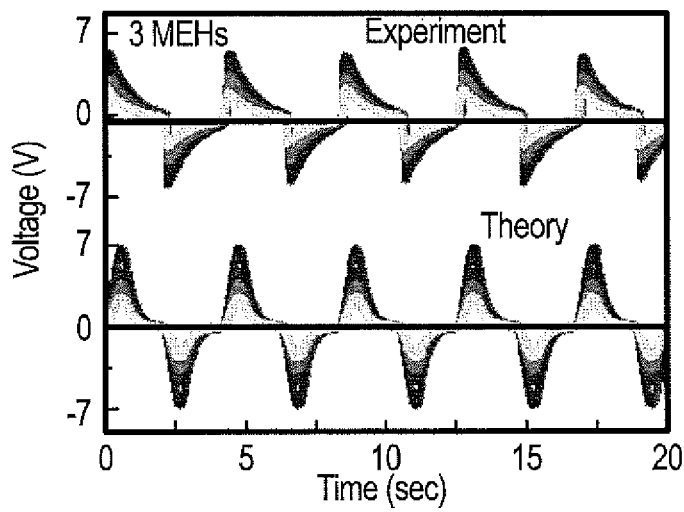
Figure 12C:
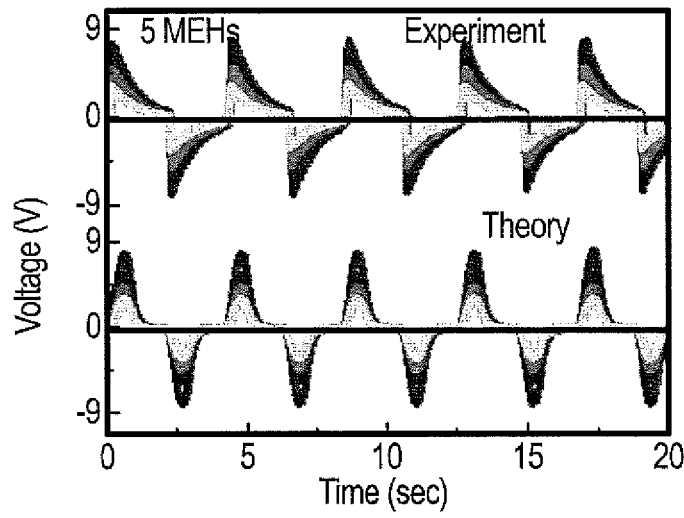
Figure 13A:
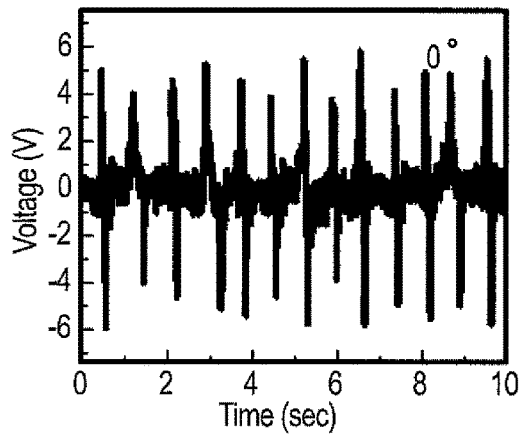
FIGS. 13A-13D are graphs illustrating in vivo evaluation of stacked PZT MEHs on voltage output. The graphs illustrate voltage as a function of time for devices that incorporate 3 layers (FIGS. 13A and 13B) and 5 layers (FIGS. 13C and 13D) of PZT MEHs connected in series and mounted in the RV of a bovine heart (80 beats/min) at 0° (left) and at 45° (right).
Figure 13B:
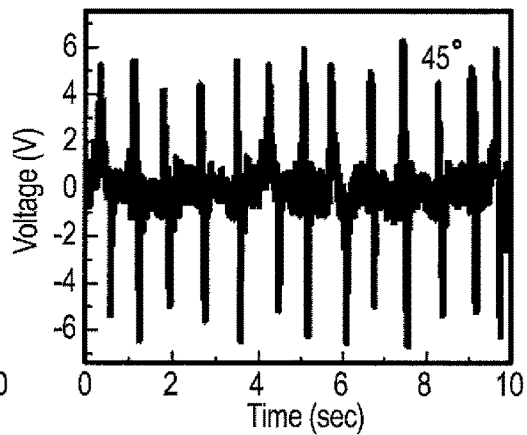
Figure 13C:
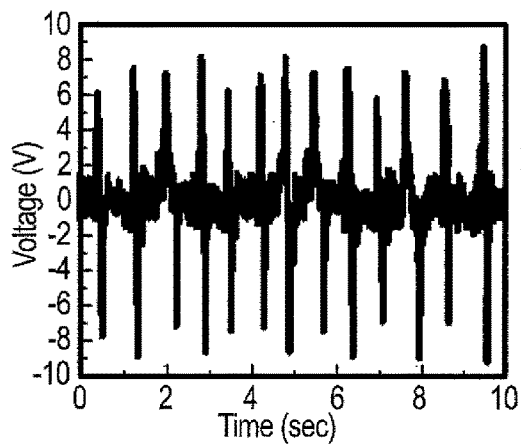
Figure 13D:
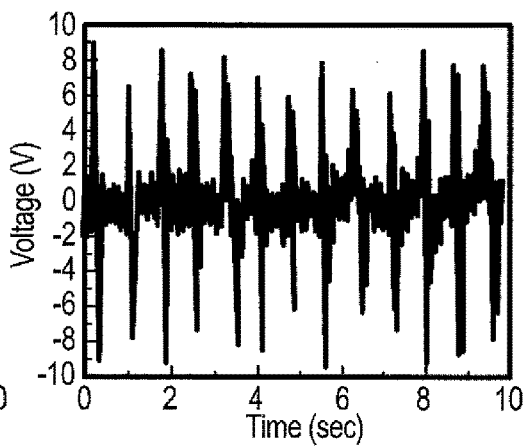

Stacking multiple PZT MEH materials (FIG. 11A) increases the power output. Consider a stack of $n_{MEH}$ PZT MEHs thin, spin-cast layers of silicone layer in between (FIG. 11B) as adhesives and strain isolating layers. The silicone, which is much more compliant (Young's modulus 60 KPa) than the PI (Young's modulus 2.5 GPa), does not significantly alter the modes of deformation of the PZT MEHs (see Table 1). As a result, for a stack of $n_{MEH}$ PZT MEHs, Eq. 5 can be applied simply by replacing N with $N*n_{MEH}$. For multilayer stacks with $n_{MEH}$=3 and 5, in vitro experiments showed peak voltages of 5.8 V and 8.1 V (FIG. 12) respectively, consistent with Eq. 5. Both values are higher than that (3.7 V) for a single layer device. The time-averaged power density increases with $n_{MEH}$, and can reach as large as 1.2 μW/cm² (FIG. 11C) for $n_{MEH}$=5, which is sufficient to operate a cardiac pacemaker.

In vivo demonstrations on the bovine heart are consistent with these results (see FIGS. 13A-13D).

We claim:

1. A system for providing energy to a device or machine comprising a stack of layers of mechanical energy harvesting materials and one or more rectifiers, filters, and/or batteries,
    wherein the stack comprises a first layer of mechanical energy harvesting materials below a second layer of mechanical energy harvesting materials,
    wherein each layer comprises a group of mechanical energy harvesting materials, wherein the mechanical energy harvesting materials in each group are connected in parallel,
    wherein each mechanical energy harvesting material comprises a flexible substrate, wherein the flexible substrate has a Young's modulus of about 0.01 to 5.0 GPa, and a plurality of piezoelectric elements,
    wherein the piezoelectric elements are in the form of ribbons, wherein each ribbon is located between a first and a second electrode, wherein the first and second electrodes are parallel to the surface of the ribbon, wherein each ribbon has a thickness, a width and a length, and wherein the piezoelectric elements are located in and/or on the flexible substrate.

2. The system of claim 1, wherein the system provides sufficient energy to power devices external or internal to the body, organ, tissue or tissue component.

3. The system of claim 1, wherein the system provides sufficient energy to power devices and systems to measure, sense, interrogate, monitor, record/capture, telemeter actuate, modfy, stimulate deliver a drug or otherwise interact with a body, organ, tissue or tissue component.

4. The system of claim 1, wherein the system provides sufficient energy to power a cardiac pacemaker.

5. The system of claim 1, wherein the system provides peak voltages of 3.8 V or greater.

6. The system of claim 1, wherein at least one layer comprises two or more groups of mechanical energy harvesting materials, wherein each group is connected to a neighboring group in series.

7. The system of claim 6, comprising at least 5 groups of mechanical energy harvesting materials.

8. The system of claim 1, having an efficiency of at least 1% for the conversion of applied mechanical stress to electrical energy.

9. The system of claim 1, wherein each mechanical energy harvesting material is configured to bend in the longitudinal direction relative to the orientation of the ribbons when placed on the surface of a device or portion of the body that provides a mechanical stress or to which a mechanical stress is applied.

10. The system of claim 1 encapsulated in a biocompatible material.

11. A method for providing energy to a biomedical device or a battery for the device comprising providing the system of claim 1 in electrical communication with the biomedical device or the battery for the device.

12. The method of claim 11, wherein the device is a cardiac pacemaker.

13. The system of claim 1, wherein the thickness of the ribbons is in the range from about 100 nm to about 10 microns.

14. The system of claim 1, comprising at least 2 ribbons.

15. The system of claim 1, comprising more than 10 ribbons.

16. The system of claim 1, further comprising a compliant material that is more compliant than the flexible substrate, wherein the compliant material is located between each layer and the adjacent layer in the stack.

17. The system of claim 1, wherein the distance (h) from the center of each ribbon to the neutral mechanical plane is sufficient to allow the flexible substrate to bend at its maximum strain, wherein the bending strain for the ribbons is smaller than the bending strain for the flexible substrate.

18. The system of claim 1, wherein the piezoelectric elements are formed of a material selected from the group consisting of Berlinite, Sucrose, Quartz, Rochelle salt, Topaz, Tourmaline-group minerals, Gallium orthophosphate, Langasite, Barium titanate, Lead titanate, Lead zirconate titanate, Potassium niobate, Lithium niobate, Lithium tantalate, Sodium tungstate, Zinc oxide, $Ba_2NaNb_5O_5$, $Pb_2KNb_5O_{15}$, Sodium potassium niobate, Bismuth ferrite, Sodium niobate, Bismuth titanate, Sodium bismuth titanate, polyvinylidene fluoride, polyRvinylidenefluoride-co-trifluoroethylend and combinations thereof.

19. The system of claim 1, wherein the flexible substrate is formed from a material selected from the group consisting of polyurethanes, silicon rubber, polyethers, polyesters, copolymers of polyether urethanes, polyester urethanes, polysulfones, polybutadiene-styrene, elastomers, hydrogels formed from copolymers of polyethylene glycol and polylactide, polyglycolide or copolymers of polylactide-co-glycolide Polyacrylate Rubber, Ethylene-acrylate Rubber, Polyester Urethane, Bromo Isobutylene Isoprene, Polybutadiene, Chloro Isobutylene Isoprene, Polychloroprene, Chlorosulphonated Polyethylene, Epichlorohydrin, Ethylene Propylene, Ethylene Propylene Diene Monomer, Polyether Urethane, Perfluorocarbon Rubber, Fluronated Hydrocarbon, Fluro Silicone, Fluorocarbon Rubber, Hydrogenated Nitrile Butadiene, Polyisoprene, Isobutylene Isoprene Butyl, Acrylonitrile Butadiene, Polyurethane, Styrene Butadiene, Styrene Ethylene Butylene Styrene Copolymer, Polysiloxane, Vinyl Methyl Silicone, Acrylonitrile Butadiene Carboxy Monomer, Styrene Butadiene Carboxy Monomer, Thermoplastic Polyether-ester, Styrene Butadiene Block Copolymer, Styrene Butadiene Carboxy Block Copolymer, Synthetic polyisoprene, Polybutadiene, Chloropene rubber, polychloropene, Neoprene, Baypren, Butyl rubber, Halogenated butyl rubbers, Styrene-butadiene Rubber, Nitrile rubber, Hydrogenated Nitrile Rubbersethylene propylene rubber, ethylene propylene diene rubber, Epichlorohydrin rubber Polyacrylic rubber, Silicone rubber, Flurosilicone Rubber, Fluorosilicone Rubber, Fluroelastomers Viton, Tecnoflon, Fluorel, Aflas and Dai-El, Perfluoroelastomers Tecnoflon PFR, Kalrez, Chemraz, Perlast, Polyether block amides, Chlorosulfonated polyethylene, Hypalon, Ethylene-vinyl acetate, and combinations thereof.

20. The system of claim 19, wherein the flexible substrate is an elastomer, and
   wherein the elastomer is selected from the group consisting of natural elastomers, thermoplastic elastomers, styrenic materials, olefenic materials, polyolefin, polyurethane thermoplastic elastomers, polyamides, synthetic rubbers, silicon-based organic polymers including polydimethylsiloxane, polybutadiene, polyisobutylene, poly(styrene-butadiene-styrene), polyurethanes, polychloroprene, silicones, Synthetic polyisoprene, Polybutadiene, Chloropene rubber, polychloropene, Neoprene, Baypren, Butyl rubber, Halogenated butyl rubbers, Styrene-butadiene Rubber, Nitrile rubber, Hydrogenated Nitrile Rubbers, ethylene propylene rubber, ethylene propylene diene rubber Epichlorohydrin rubber Polyacrylic rubber, Silicone rubber, Flurosilicone Rubber, Fluorosilicone Rubber, Fluroelastomers Viton, Tecnoflon, Fluorel, Aflas and Dai-El, Perfluoroelastomers Tecnoflon PFR, Kalrez, Chemraz, Perlast, Polyether block amides, Chlorosulfonated polyethylene, Hypalon, Ethylene-vinyl acetate, and combinations thereof.

21. The system of claim 1, further comprising a second substrate with a Young's modulus that is greater than 10 GPa.

* * * * *

UNITED STATES PATENT AND TRADEMARK OFFICE
CERTIFICATE OF CORRECTION

PATENT NO. : 10,137,306 B2
APPLICATION NO. : 15/111447
DATED : November 27, 2018
INVENTOR(S) : Canan Dagdeviren, John A. Rogers and Marvin J. Slepian It is certified that error appears in the above-identified patent and that said Letters Patent is hereby corrected as shown below:

In the Specification

Column 12, Lines 31-32, replace "poly[(vinylidenefluoride-co-trifluoroethylene]" with --poly(vinylidenefluoride-co-trifluoroethylene)--.

In the Claims

Claim 18, Column 31, Lines 19-20, replace "polyRvinylidenefluoride-co-trifluoroethylend" with --poly(vinylidenefluoride-co-trifluoroethylene)--.

Signed and Sealed this
Twenty-first Day of May, 2019

Andrei Iancu
*Director of the United States Patent and Trademark Office*